United States Patent
Dhau et al.

(10) Patent No.: US 12,343,680 B2
(45) Date of Patent: Jul. 1, 2025

(54) FLUID FILTRATION SYSTEM AND METHOD OF USE

(71) Applicant: Molekule Group, Inc., Palm Beach, FL (US)

(72) Inventors: Jaspreet S. Dhau, San Francisco, CA (US); David Sanabria, San Francisco, CA (US); Dilip N. Goswami, San Francisco, CA (US)

(73) Assignee: Molekule Group, Inc., Palm Beach Gardens, FL (US)

( * ) Notice: Subject to any disclaimer, the term of this patent is extended or adjusted under 35 U.S.C. 154(b) by 784 days.

(21) Appl. No.: 17/520,598

(22) Filed: Nov. 5, 2021

(65) Prior Publication Data

US 2022/0062822 A1 Mar. 3, 2022

Related U.S. Application Data

(63) Continuation-in-part of application No. 17/152,690, filed on Jan. 19, 2021, now abandoned.
(Continued)

(51) Int. Cl.
*B01D 53/88* (2006.01)
*A61L 9/20* (2006.01)
(Continued)

(52) U.S. Cl.
CPC ......... *B01D 53/885* (2013.01); *B01D 53/007* (2013.01); *B01D 53/94* (2013.01);
(Continued)

(58) Field of Classification Search
CPC .... B01D 53/885; B01D 53/007; B01D 53/94; B01D 53/0407; B01D 2255/802;
(Continued)

(56) References Cited

U.S. PATENT DOCUMENTS

| 2,311,272 A | 2/1943 | Ware |
| 4,065,276 A | 12/1977 | Nakaya et al. |

(Continued)

FOREIGN PATENT DOCUMENTS

| CA | 3095953 A1 * | 10/2019 | ............... A61L 9/20 |
| CN | 102794039 A | 11/2012 | |

(Continued)

OTHER PUBLICATIONS

"Molekule Air Purifier found online—[Feb. 22, 2018]—https://molekule.com/?utm_source=google_search_search&utm_medium=rt&utm_campaign=brand&utm_term=term=molekule&utm_content=bmm_2&gclid=EAalQobChMl5ufdtbK62QIViYjlCh3d8gvEAYAASAAEgJcdPD_BwE".

(Continued)

*Primary Examiner* — Edelmira Bosques
*Assistant Examiner* — Frances F. Hamilton
(74) *Attorney, Agent, or Firm* — Jeffrey Schox; Randy Mehlenbacher

(57) ABSTRACT

A system comprising a housing; a filter retained within the housing; an activation mechanism configured to, during operation, activate the filter; and a flow controller configured to urge fluid through the filter. The activation mechanism functions to emit at least a threshold amount, or less, of energy or energy density, a predetermined energy or energy density, and/or any suitable amount of energy and/or energy density to activate the filter and remove contaminants.

22 Claims, 15 Drawing Sheets

Related U.S. Application Data

(60) Provisional application No. 63/222,815, filed on Jul. 16, 2021, provisional application No. 63/033,538, filed on Jun. 2, 2020, provisional application No. 62/968,715, filed on Jan. 31, 2020, provisional application No. 62/962,792, filed on Jan. 17, 2020.

(51) Int. Cl.
   *B01D 53/00* (2006.01)
   *B01D 53/94* (2006.01)
   *B01J 35/39* (2024.01)
   *F24F 8/22* (2021.01)

(52) U.S. Cl.
   CPC ............ *B01J 35/39* (2024.01); *F24F 8/22* (2021.01); *A61L 9/205* (2013.01); *B01D 2255/802* (2013.01)

(58) Field of Classification Search
   CPC ....... B01D 2259/804; B01J 35/39; F24F 8/22; A61L 9/205
   USPC ............................................. 422/186
   See application file for complete search history.

(56) References Cited

U.S. PATENT DOCUMENTS

| | | |
|---|---|---|
| 4,896,590 A | 1/1990 | Groos |
| 4,931,654 A | 6/1990 | Horng |
| D328,946 S | 8/1992 | Havrilla |
| D360,635 S | 7/1995 | Mark |
| D362,441 S | 9/1995 | Mark |
| 5,453,049 A | 9/1995 | Tillman et al. |
| 5,505,904 A | 4/1996 | Haidinger et al. |
| 5,620,669 A | 4/1997 | Plinke et al. |
| 5,790,934 A | 8/1998 | Say et al. |
| D400,663 S | 11/1998 | Furlough |
| 5,873,920 A | 2/1999 | Wong et al. |
| 5,922,093 A | 7/1999 | James et al. |
| 5,933,702 A * | 8/1999 | Goswami .............. F24F 3/12 422/186.3 |
| 6,531,100 B1 | 3/2003 | Ogata et al. |
| 6,607,702 B1 | 8/2003 | Kang et al. |
| 6,613,277 B1 | 9/2003 | Monagan |
| D493,874 S | 8/2004 | Woods |
| D505,999 S | 6/2005 | Song |
| 6,939,397 B2 | 9/2005 | Nelsen et al. |
| 7,063,820 B2 | 6/2006 | Goswami |
| 7,074,369 B2 | 7/2006 | Tabatabaie-Raissi et al. |
| 7,160,506 B2 | 1/2007 | Deshpande |
| D552,724 S | 10/2007 | Chen |
| 7,291,205 B2 * | 11/2007 | Chu .............. B01D 53/261 55/471 |
| 7,371,351 B2 | 5/2008 | Goswami |
| 7,566,359 B2 | 7/2009 | Goel et al. |
| D611,579 S | 3/2010 | Zlotnik et al. |
| 7,820,100 B2 | 10/2010 | Garfield et al. |
| 7,910,940 B2 | 3/2011 | Koike et al. |
| 8,003,058 B2 | 8/2011 | Bergeron et al. |
| D648,429 S | 11/2011 | Choi et al. |
| D652,408 S | 1/2012 | Chen |
| D687,017 S | 7/2013 | Ashcraft et al. |
| D697,496 S | 1/2014 | Ashcraft et al. |
| 8,658,046 B2 | 2/2014 | Barry et al. |
| 8,709,341 B2 | 4/2014 | Day et al. |
| D710,329 S | 8/2014 | Holzer |
| D716,427 S | 10/2014 | Lim et al. |
| D717,420 S | 11/2014 | Von Seggern |
| 8,951,376 B2 | 2/2015 | Rasmussen |
| D744,541 S | 12/2015 | Langhammer et al. |
| D752,732 S | 3/2016 | Ansley et al. |
| D754,832 S | 4/2016 | Seo et al. |
| D766,213 S | 9/2016 | Hinokio |
| D768,844 S | 10/2016 | Koseoglu et al. |
| D773,704 S | 12/2016 | Pardo et al. |
| D774,020 S | 12/2016 | Hinokio |
| 9,662,626 B2 | 5/2017 | Yates et al. |
| D796,019 S | 8/2017 | Thompson |
| D802,022 S | 11/2017 | Yao et al. |
| D803,369 S | 11/2017 | Kim et al. |
| D803,810 S | 11/2017 | Lee et al. |
| D804,002 S | 11/2017 | Huang |
| D805,622 S | 12/2017 | Lee |
| D806,843 S | 1/2018 | McDonnell |
| D807,327 S | 1/2018 | Xiong |
| D808,927 S | 1/2018 | Schaal et al. |
| D810,049 S | 2/2018 | Lee et al. |
| D810,135 S | 2/2018 | Langhammer et al. |
| D810,137 S | 2/2018 | Tsang et al. |
| D810,265 S | 2/2018 | Chen |
| D810,266 S | 2/2018 | Li |
| D818,097 S | 5/2018 | Cho et al. |
| 10,039,852 B2 | 8/2018 | Yi et al. |
| D828,912 S | 9/2018 | Powell et al. |
| D829,312 S | 9/2018 | Riering-Czekalla et al. |
| D829,313 S | 9/2018 | Cho et al. |
| D829,314 S | 9/2018 | Cho et al. |
| D831,810 S | 10/2018 | Cho et al. |
| D831,811 S | 10/2018 | Cho et al. |
| D832,414 S | 10/2018 | Sharma et al. |
| 10,105,463 B2 | 10/2018 | Kim et al. |
| D834,694 S | 11/2018 | Walter et al. |
| 10,137,216 B2 | 11/2018 | Goswami et al. |
| D835,766 S | 12/2018 | Chen |
| D836,760 S | 12/2018 | Fredäng et al. |
| 10,183,187 B2 | 1/2019 | Li |
| D850,596 S | 6/2019 | Wu |
| D865,149 S | 10/2019 | Lin |
| D865,932 S | 11/2019 | Ha et al. |
| D870,870 S | 12/2019 | Copparstad et al. |
| 10,517,980 B2 * | 12/2019 | Kim .................... B01D 53/885 |
| D879,276 S | 3/2020 | King |
| D884,138 S | 5/2020 | Chen |
| D884,860 S | 5/2020 | Zhang |
| D886,268 S | 6/2020 | Montagnino et al. |
| D886,272 S | 6/2020 | Yang et al. |
| 10,684,027 B2 | 6/2020 | Goswami et al. |
| 10,933,159 B2 * | 3/2021 | Benedek ................. A61L 9/205 |
| 10,981,102 B2 | 4/2021 | Trent et al. |
| 11,097,525 B1 | 8/2021 | Dhau et al. |
| 11,596,900 B2 | 3/2023 | Dhau et al. |
| 2002/0160913 A1 | 10/2002 | Sangiovanni et al. |
| 2003/0180200 A1 | 9/2003 | Reisfeld |
| 2004/0007000 A1 | 1/2004 | Takeda et al. |
| 2004/0013583 A1 * | 1/2004 | Burkhardt ........... B01D 53/885 422/186.3 |
| 2004/0146437 A1 | 7/2004 | Arts et al. |
| 2004/0166037 A1 * | 8/2004 | Youdell ................ A61L 9/205 422/186.3 |
| 2004/0262217 A1 | 12/2004 | Mori et al. |
| 2005/0061656 A1 | 3/2005 | Benoit et al. |
| 2005/0129591 A1 | 6/2005 | Wei et al. |
| 2005/0138905 A1 | 6/2005 | Kubokawa |
| 2005/0193696 A1 | 9/2005 | Muller et al. |
| 2005/0201907 A1 | 9/2005 | Wakamura |
| 2006/0057020 A1 * | 3/2006 | Tufo ....................... F24F 8/22 422/24 |
| 2006/0124442 A1 | 6/2006 | Valpey et al. |
| 2006/0150818 A1 | 7/2006 | Okamoto et al. |
| 2006/0188388 A1 * | 8/2006 | Goswami ................ A61L 2/02 422/28 |
| 2007/0041882 A1 | 2/2007 | Roseberry et al. |
| 2007/0059225 A1 | 3/2007 | Willette |
| 2007/0199288 A1 | 8/2007 | Paterson et al. |
| 2007/0213002 A1 * | 9/2007 | Okamoto ............... B01J 35/40 502/100 |
| 2007/0253860 A1 | 11/2007 | Schroder |
| 2007/0289270 A1 | 12/2007 | Schumann et al. |
| 2008/0050288 A1 | 2/2008 | Okamoto et al. |
| 2008/0112845 A1 | 5/2008 | Dunn et al. |
| 2009/0002985 A1 | 1/2009 | Peck et al. |
| 2009/0010801 A1 | 1/2009 | Murphy et al. |
| 2009/0032390 A1 | 2/2009 | Osterlund |

(56) References Cited

U.S. PATENT DOCUMENTS

| | | |
|---|---|---|
| 2009/0175757 A1 | 7/2009 | Yao et al. |
| 2009/0229478 A1 | 9/2009 | Wu |
| 2009/0245594 A1 | 10/2009 | Abramovich et al. |
| 2010/0003164 A1 | 1/2010 | Bourne et al. |
| 2010/0101413 A1 | 4/2010 | Jones et al. |
| 2010/0143205 A1 | 6/2010 | Engelhard |
| 2010/0196222 A1 | 8/2010 | Kosugi et al. |
| 2010/0196223 A1 | 8/2010 | Hay et al. |
| 2010/0260644 A1 | 10/2010 | Day et al. |
| 2010/0303678 A1 | 12/2010 | Lockhart et al. |
| 2011/0088375 A1 | 4/2011 | Suzuki et al. |
| 2011/0101712 A1* | 5/2011 | LaConte .............. E05C 19/022 292/300 |
| 2011/0117002 A1 | 5/2011 | Dardas et al. |
| 2011/0203238 A1 | 8/2011 | Witter et al. |
| 2012/0063958 A1 | 3/2012 | Riviere et al. |
| 2012/0183443 A1 | 7/2012 | Hurley |
| 2012/0199005 A1 | 8/2012 | Koji et al. |
| 2012/0273340 A1 | 11/2012 | Felix |
| 2013/0036908 A1 | 2/2013 | Jones et al. |
| 2013/0294968 A1 | 11/2013 | Owen et al. |
| 2014/0271419 A1 | 9/2014 | Tsotsis et al. |
| 2014/0290489 A1 | 10/2014 | Uemura et al. |
| 2015/0008014 A1 | 1/2015 | Zhou et al. |
| 2015/0125355 A1 | 5/2015 | Lee et al. |
| 2015/0306271 A1 | 10/2015 | Willette |
| 2015/0320900 A1* | 11/2015 | Goswami .......... B01D 53/8668 422/122 |
| 2015/0375187 A1* | 12/2015 | Yates ...................... B01J 8/008 423/230 |
| 2016/0129432 A1* | 5/2016 | Ozaki .................... B01J 37/349 502/309 |
| 2016/0236129 A1* | 8/2016 | Ajemian ................ B01D 53/75 |
| 2016/0279556 A1 | 9/2016 | Law |
| 2017/0043044 A1 | 2/2017 | Sobhy |
| 2017/0106218 A1 | 4/2017 | Lin et al. |
| 2017/0122605 A1 | 5/2017 | Lee et al. |
| 2017/0273845 A1 | 9/2017 | Phillips et al. |
| 2017/0321717 A1 | 11/2017 | Park et al. |
| 2018/0001312 A1 | 1/2018 | Shibai et al. |
| 2018/0027809 A1 | 2/2018 | Chiattello et al. |
| 2018/0104374 A1 | 4/2018 | Kim et al. |
| 2018/0117511 A1 | 5/2018 | Yamauchi et al. |
| 2018/0169551 A1 | 6/2018 | Jaganathan et al. |
| 2018/0339073 A1* | 11/2018 | Clynne ................. A61L 2/0047 |
| 2018/0344890 A1 | 12/2018 | Watanabe et al. |
| 2019/0063763 A1* | 2/2019 | Kleinberger ......... B01D 46/521 |
| 2019/0083674 A1* | 3/2019 | Jeong ..................... A61L 9/205 |
| 2019/0083930 A1 | 3/2019 | Bernardoni et al. |
| 2019/0113246 A1 | 4/2019 | Goswami et al. |
| 2019/0120508 A1 | 4/2019 | Goswami et al. |
| 2019/0126202 A1* | 5/2019 | Rao ...................... B01D 53/885 |
| 2019/0314751 A1 | 10/2019 | Cheng et al. |
| 2020/0030731 A1* | 1/2020 | Dhau ................. B01D 53/0407 |
| 2020/0061231 A1* | 2/2020 | Jeong .................... B01D 46/64 |
| 2020/0061635 A1 | 2/2020 | Wiser et al. |
| 2020/0109869 A1 | 4/2020 | Mäkipää et al. |
| 2020/0129972 A1 | 4/2020 | Ozaki et al. |
| 2020/0182495 A1 | 6/2020 | Park et al. |
| 2020/0355378 A1* | 11/2020 | Jeong .................. B01D 46/645 |
| 2020/0360858 A1 | 11/2020 | Mathur et al. |
| 2021/0100924 A1* | 4/2021 | Li ........................... A61L 9/014 |
| 2021/0222897 A1 | 7/2021 | Sanabria et al. |
| 2021/0237419 A1* | 8/2021 | Dhau ................. B32B 37/1284 |
| 2021/0379220 A1 | 12/2021 | Dhau et al. |
| 2022/0032225 A1* | 2/2022 | Kim .......................... F24F 8/80 |
| 2022/0062822 A1 | 3/2022 | Dhau et al. |
| 2024/0042418 A1 | 2/2024 | Dhau et al. |

FOREIGN PATENT DOCUMENTS

| | | | |
|---|---|---|---|
| CN | 204730343 U | * 10/2015 | |
| CN | 105126836 A | 12/2015 | |
| CN | 106039994 A | * 10/2016 | ............ B01D 53/32 |
| CN | 107096320 A | 8/2017 | |
| CN | 107344043 A | 11/2017 | |
| CN | 109078493 A | * 12/2018 | |
| JP | H0568820 A | 3/1993 | |
| JP | H0668820 U | 9/1994 | |
| JP | 10-085558 A | 4/1998 | |
| JP | H11505746 A | 5/1999 | |
| JP | H11188085 A | 7/1999 | |
| JP | 2001025668 A | 1/2001 | |
| JP | 2001029441 A | 2/2001 | |
| JP | 2001232154 A | 8/2001 | |
| JP | 2002263175 A | 9/2002 | |
| JP | 2002291856 A | 10/2002 | |
| JP | 2003062414 A | 3/2003 | |
| JP | 2003070885 A | 3/2003 | |
| JP | 2007190533 A | 8/2007 | |
| JP | 2008522822 A | 7/2008 | |
| JP | 2016084946 A | 5/2016 | |
| JP | 2016530908 A | 10/2016 | |
| JP | 2017148484 A | 8/2017 | |
| KR | 19990021845 A | 3/1999 | |
| KR | 20130125190 A | 11/2013 | |
| KR | 20180057394 A | 5/2018 | |
| KR | 101977573 B1 | 5/2019 | |
| WO | 9637281 A1 | 11/1996 | |
| WO | 2004078320 A1 | 9/2004 | |
| WO | 2006065491 A2 | 6/2006 | |
| WO | 2015068520 A1 | 5/2015 | |
| WO | 2015098386 A1 | 7/2015 | |

OTHER PUBLICATIONS

Evans, Hugh. Adhesives: Understanding adhesives for filter fabrication. Apr. 26, 2012. https://www.filtsep.com/filter%,20media/ features/adhesives-understanding-adhesives-for-filter/ (Year: 2012).

Samburova, Vera , et al., "Dominant volatile organic compounds (VOCs) measured at four Cannabis growing facilities: Pilot study results", Journal of the Air & Waste Management Association, Sep. 9, 2019.

"Molekule Website Screen Capture from Jun. 10, 2016 by Wayback Machine, (Year: 2016)".

"Water-Based Adhesives-Information and Overview", https://www.hotmelt.com/blogs/blog/water-based-adhesives-information-and-overview.

Curtis, Gannon L., et al., "Reduction of Total and Viable Air Particles in the OR Setting by using Ultraviolet In-room Air Disinfection and Recirculation Units", American Association of Hip and Knee Surgeons, Cleveland Clinic, Nov. 4, 2017.

Hou, Wenbo , et al., A review of surface plasmon resonance-enhanced photocatalysis, Advanced 4, 15 Functional Materials 23.13 (Apr. 5, 2013): 1612-1619. p. 1 col. 2 para 1, p. 2 col. 1 para 2.

Merrill, Reynold C., et al., "Chemistry of the soluble silicates", J. Chem. Educ. 1947, 24, 6, 262, Jun. 1, 1947, https://pubs.acs.org/doi/pdf/10.1021/ed024p262.

Ochiai, Tsuyoshi , et al., Photoelectrochemical properties of TiO2 photocatalyst and its applications for environmental purification, Journal of Photochemistry and Photobiology C: Photochemistry reviews 13.4 (Dec. 1, 2012): 247-262.

\* cited by examiner

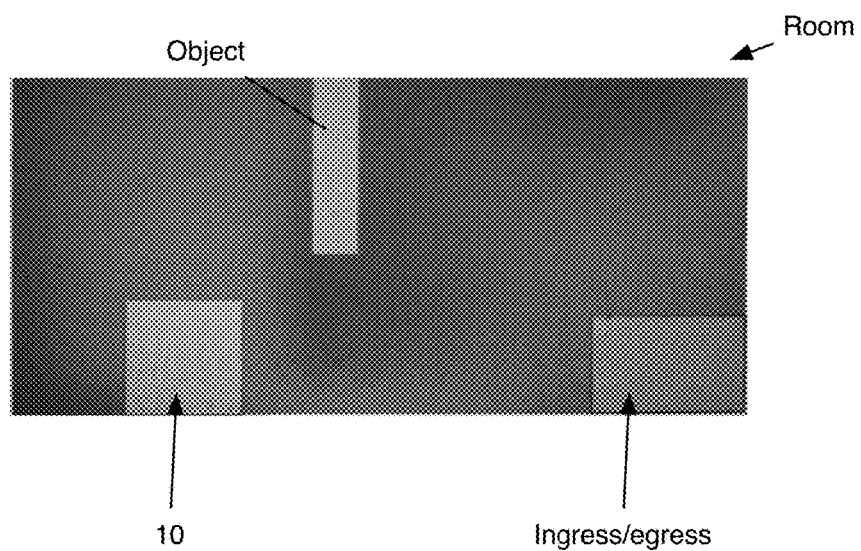
FIGURE 3
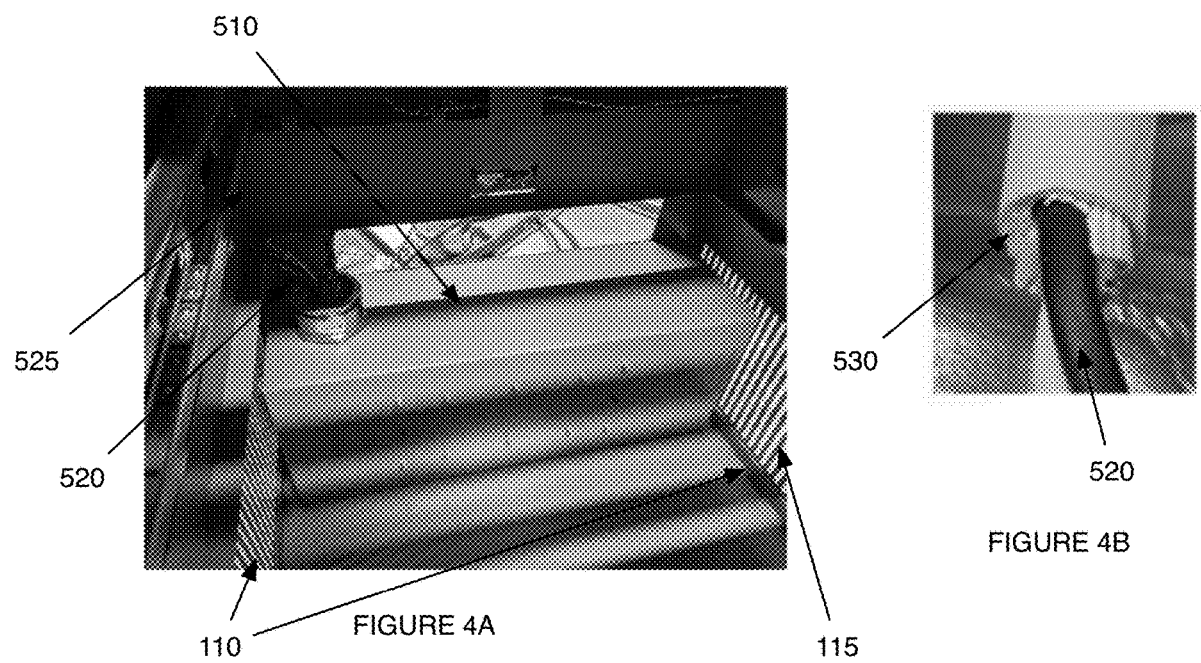
FIGURE 4A
FIGURE 4B

FLUID FILTRATION SYSTEM AND METHOD OF USE

CROSS-REFERENCE TO RELATED APPLICATIONS

This application is a continuation-in-part of U.S. patent application Ser. No. 17/152,690, filed 19 Jan. 2021, which claims the benefit of U.S. Provisional Application No. 62/962,792, filed 17 Jan. 2020; U.S. Provisional Application No. 62/968,715, filed 31 Jan. 2020; and U.S. Provisional Application No. 63/033,538, filed 2 Jun. 2020, each of which is incorporated in its entirety by this reference.

This application also claims benefit to U.S. Provisional Application No. 63/222,815 filed 16 Jul. 2021, which is incorporated in its entirety by this reference.

TECHNICAL FIELD

This invention relates generally to the fluid purification field, and more specifically to a new and useful system and method of use in the fluid purification field.

BACKGROUND

Many healthcare and industrial settings (e.g., operating rooms, clean rooms, etc.) require clean air (e.g., air that has pathogens, allergens, dust particles, VOCs, and/or other contaminants below a contaminant threshold). Typically, clean air is provided using a building air filtration system (e.g., HVAC). However, these building wide air filtration systems can become dirty releasing more particulate matter over time, can transfer contamination from other parts of the building, and may not be equipped to adjust to contaminants introduced during the ingress/egress of individuals into an area. Having a dedicated unit for a given room and/or area may help to alleviate these concerns.

Thus, there is a need in the air purification field to create a new and useful air filtration system. This invention provides such new and useful air filtration system and method of use.

BRIEF DESCRIPTION OF THE FIGURES

FIG. 3 is a schematic representation of an example of a cross-sectional view of CFD analysis of fluid flow within a space based on the position of the fluid filtration system.
FIGS. 4A, 4B, and 4C are schematic representations of examples of a power supply housing.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
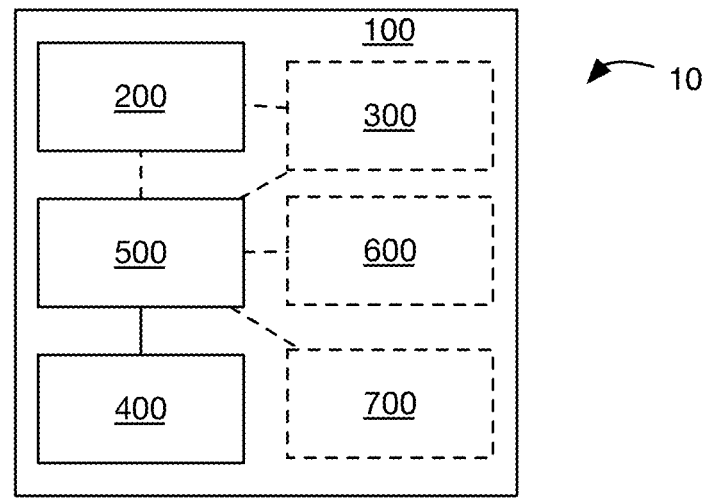
FIG. 1 is a schematic representation of the system.

As shown in FIG. 1, the system 10 preferably includes a housing 100, one or more filters 200, a flow control mechanism 400, and a power supply 500. The system can include one or more activation mechanisms 300, one or more sensors 600, a user interface 700, and/or any suitable components. The system preferably functions to filter fluid (e.g., air, liquids, etc.) within an area to remove (e.g., capture, degrade, etc.) contaminants from the fluid. In specific examples, the contaminants can include: pathogens (e.g., bacteria, viruses, etc.), fungi (e.g., mold, mildew, etc.), allergens (e.g., dander, pollen, dust mites, etc.), particulate matter (e.g., dust, smoke, droplets, etc.), volatile compounds (e.g., volatile organic compounds (VOCs); dioxins; furans; aromatic compounds; oxides of nitrogen; oxides of sulfur; oxides of phosphorus; biogenic VOCs such as isoprene, terpenes, monoterpenes, sesquiterpenes, myrcene, limonene, terpinolene, α-pinene, β-pinene, camphene, ocimene, carene, etc.; etc.), inorganic compounds, and/or any suitable contaminant.

In an embodiment of the technology, the system can be used in a hospital operating room (and/or other critical environments such as isolation units, emergency rooms, waiting rooms, intensive care units, etc.). Within operating rooms, it is common to have air curtains surrounding patients during the operation to help minimize patient exposure to pathogens and dirt from the environment. In this example, the technology can be used to filter air within the operating room to help improve the sterility of the environment, can filter the air that is used to prepare the air curtain (e.g., an output of the air filtration system can be coupled to an air intake for the air curtain), and/or can be used in any suitable manner. In variants of this embodiment, as shown in FIG. 3, the system location within the room can be selected (e.g., using computational fluid dynamics (CFD) analysis of a room) based on the air curtain (e.g., to minimally perturb the air curtain), to output filtered air on the patient, to capture contaminants within the room (e.g., from ingress and/or egress points to the room), and/or can be positioned in any suitable manner. However, the technology can additionally or alternatively be used in industrial centers (e.g., clean rooms, office spaces, etc.), food processing plants, veterinary practices, and/or in any suitable applications. For example, the technology can be used to purify air (or other fluids) within the tanning industry (e.g., leather tanning such as to remove VOCs or dead cells), animal shelters, veterinarian offices, paint shops, kitchens (e.g., restaurant kitchens, catering kitchens, bakeries, etc.), 3D printing facilities, fuel storage areas, carpentry shops, grow rooms (e.g., marijuana grow rooms), curing rooms (e.g., marijuana curing rooms), dispensaries, green houses, and/or in any suitable space or application.

2. Benefits

Variations of the technology can confer several benefits and/or advantages.

First, variants of the technology can be used to remove biologically active contaminants (e.g., pathogens, aeroallergens, fungi, fungal fragments, proteins, etc.). Examples of the technology can reduce the concentration of biologically active contaminants to a safe limit for occupants of the area (e.g., immunocompromised occupants). The inventors have discovered that including an antibiological prefilter can, in some variants of the technology, enhance (e.g., improve, facilitate, speed up, etc.) the removal of biologically active contaminants. In a specific example, the antibiological prefilter can include photocatalytic material (e.g., the same or a different photocatalytic material as a photocatalytic filter). In this specific example the antibiological prefilter can be substantially unilluminated (e.g., be illuminated by less than a threshold irradiance, less than a threshold photon flux, etc.; be indirectly illuminated such as from diffuse or specular reflections as opposed to direct illumination from a source; etc.) or illuminated.

Second, variants of the technology can be modular to enable the system to be modified for cleaning in a specific area (e.g., to address different contaminants in different areas, at different times, etc.). In a specific example, the technology can use (e.g., interchange between) type, number, orientation, relative order, etc. the filters and/or activation mechanisms within the system (e.g., depending on the application, contaminants, filtration efficiency, target flow rate, etc.).

Third, variants of the technology can be readily rearranged within an area. In specific examples, the technology can be repositioned, reoriented, and/or removed (or brought into) an area or space.

Fourth variants of the technology can extend a lifetime or decrease a frequency of filter maintenance. For example, using a cascade of filters (e.g., progressively higher efficiency such as photodegradation efficiency, photocatalytic efficiency, mechanical efficiency, etc.) within an air filtration system can remove (e.g., capture, degrade, oxidize, etc.) polyaromatic hydrocarbons (PAHs, such as those released during wildfires), VOCs, biogenic toxins, aeroallergens, and larger particulates (e.g., organic or inorganic particulates such as pet dander, hair, dust, pollens etc.) from the fluid stream so that they do not overwhelm, saturate, block, and/or otherwise reach or impact downstream filters.

However, variants of the technology can confer any other suitable benefits and/or advantages.

3. System

The system 10 preferably functions to remove one or more contaminants from fluid (e.g., solids such as pet dander, gases such as air; liquids such as oil, water, etc.; etc.) within an environment (e.g., an enclosed environment, an open environment, etc.). The system can intake fluid from an environment proximal the system (e.g., an environment outside the housing), an input system, and/or otherwise intake the (contaminated) fluid. The system can eject purified fluid (e.g., fluid with a lower contaminant concentration than the intake fluid) into the environment, an output system (such as an air curtain generator, an HVAC system, ventilation ducts, etc.), and/or otherwise eject purified fluid. The purified fluid preferably has a contaminant reduction (e.g., a reduced contaminant level compared to the input fluid, a contaminant level compared to an inactive control system operated for a comparable duration, etc.) that is at least 90% such as 95%, 97.5%, 98%, 99%, 99.9%, 99.99%, 99.998%, 99,999%, 99.9995%, 99.9999%, or 99.99999%. For example, the fluid filtration system can reduce a contaminant concentration from between about 100 and 100000 $\mu g/m^3$ to between about 1 ppt (part per trillion) and 1 ppm. In a second specific example, the purified air can include a volatile organic compound (VOC) concentration that is at most 10% of a VOC concentration in the contaminant-laden air. However, the contaminant reduction can be less than 90% (e.g., 10%, 20%, 30%, 50%, 75%, etc.) and/or any suitable percentage. The contaminant reduction can be for a single pass (e.g., cycling a single fluid purification volume through the system), multi-pass, after a predetermined amount of time (e.g., 1 minute, 10 minutes, 30 minutes, 1 hour, 2 hours, 4 hours, 8 hours, 12 hours, 24 hours, etc.), and/or in any suitable conditions. In an illustrative example, after operating the system for approximately 1 hour, more than 99.9% of contaminants can be destroyed. The contaminant destruction can depend on the size of the environment, the contaminant concentration, the filter(s) in the system, the activation mechanism (e.g., type, energy, power, wavelength, etc.), the photocatalyst material, the operation time, the location of the system within the environment, and/or depend on or be independent of any suitable properties.

The system can be mobile (e.g., human-movable, cartable, etc.), configured to statically mount to the environment, or otherwise configured. In examples, the system can be less than a target weight (e.g., less than 25 lbs, 50 lbs, 100 lbs, 200 lbs, 500 lbs, 1000 lbs, etc.), have one or more dimensions (e.g., lateral, longitudinal, height, etc.) smaller than a threshold size (e.g., less than 1 ft, 2 ft, 3 ft, 5 ft, 10 ft, etc.), have a housing translation system 160 (e.g., wheels, treads, transportation mechanism, etc.), and/or can have any suitable size and/or components to facilitate repositioning and/or reorientation of the system.

A fluid flow rate through the system is preferably between about 1-1000 cubic feet per minute (CFM) (e.g., 10 CFM, 20 CFM, 30 CFM, 50 CFM, 100 CFM, 200 CFM, 300 CFM, 400 CFM, 500 CFM, 600 CFM, 700 CFM, 800 CFM, 900 CFM, values or ranges therebetween, etc.), but can be less than 1 CFM, greater than 1000 CFM, or any value. The fluid flow rate can refer to a volumetric flow rate, a mass flow rate, and/or any suitable flow rate.

The system preferably includes a housing 100. The housing functions to retain one or more components, and can optionally function to cooperatively create a fluid seal with one or more of the system components. The housing can additionally function to define a fluid flow path. The housing can define a lumen (e.g., hollow cavity, fluid purification volume, air purification volume, liquid purification volume, etc.) configured to retain system components. The filter(s) 200, activation mechanism(s) 300, flow control mechanism 400, sensor(s) 600, user interface 700, power supply 500, and/or any suitable components are preferably coupled to (e.g., mounted in) the housing, but can be separate from the housing (and/or system). The housing 100 can have any suitable form factor. For example, the housing can be polygonal (e.g., rectangular prism, square prism, triangular prism, pentagonal prism, etc.), cylindrical, hemispherical, pyramidal, conical and/or have any suitable structure. The housing is preferably made of an antimicrobial, hydrophilic material (or includes a coating with such properties), but can additionally or alternatively include: metals, polymers (e.g., with less than a predetermined pore size), and/or any other suitable material. The housing preferably defines one or more inlets 110 and one or more outlets 120. However, the inlet and outlet can be the same and/or can be defined in any suitable manner.

Figure 14:
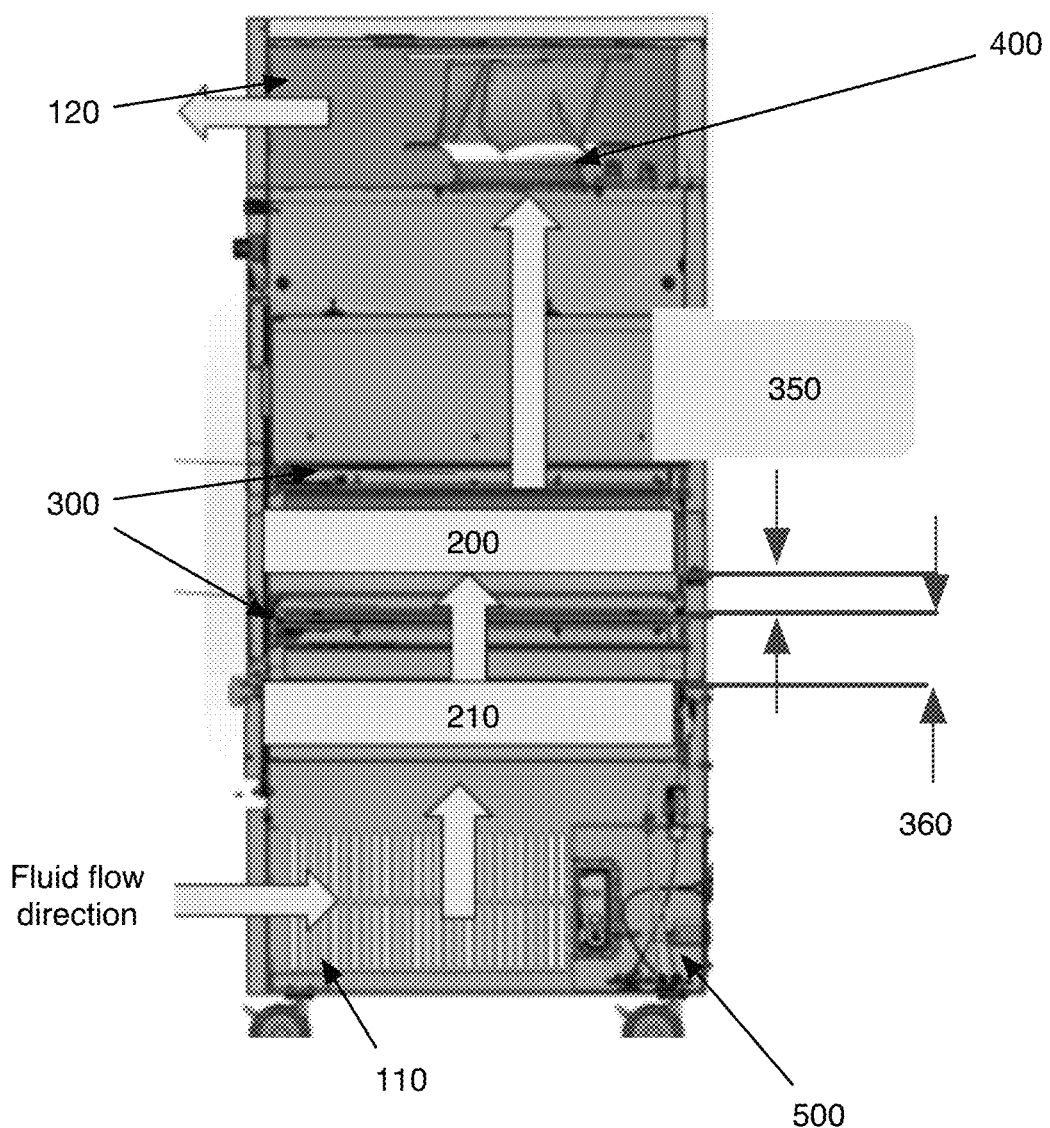
FIG. 14 is a schematic example of the system.

The inlet(s) 110 preferably functions to intake air from the surrounding environment (and/or from an external system). The inlet(s) are preferably arranged distal the active flow control mechanism, but the inlet can be arranged proximal the active flow control mechanism and/or have any suitable position relative to the active flow control mechanism. The inlet(s) are preferably arranged proximal (e.g., near, within a target distance of, within a threshold distance of, closer to, etc.) a first end of the housing (e.g., on one or more broad faces of the housing having a surface normal perpendicular to the gravity vector, on one or more broad faces of the housing having surface normal parallel to the gravity vector, etc.), but can additionally or alternatively be centrally located (e.g., approximately equidistant from the first and a second end opposing the first end of the housing), and/or be arranged at any suitable location of the housing. In an illustrative example as shown in FIG. 14, the inlets can be arranged proximal a bottom of the housing. However, the inlets can be arranged proximal the top of the housing and/or otherwise be arranged. The inlet(s) can include vents 115, openings, holes, and/or any suitable pathway allowing air to enter and/or be drawn into the system. As shown for example in FIG. 8, the inlet can be arranged around any suitable angular extent between 0°-360° of the housing. In a first specific example, the inlet can be arranged along a single broad face of the housing (e.g., 90° for a rectangular housing). In a second specific example, the inlet can be arranged along three broad faces of the housing (e.g., 270° for a rectangular housing). However, inlets can be included on any suitable broad faces of the housing.

Figure 8:
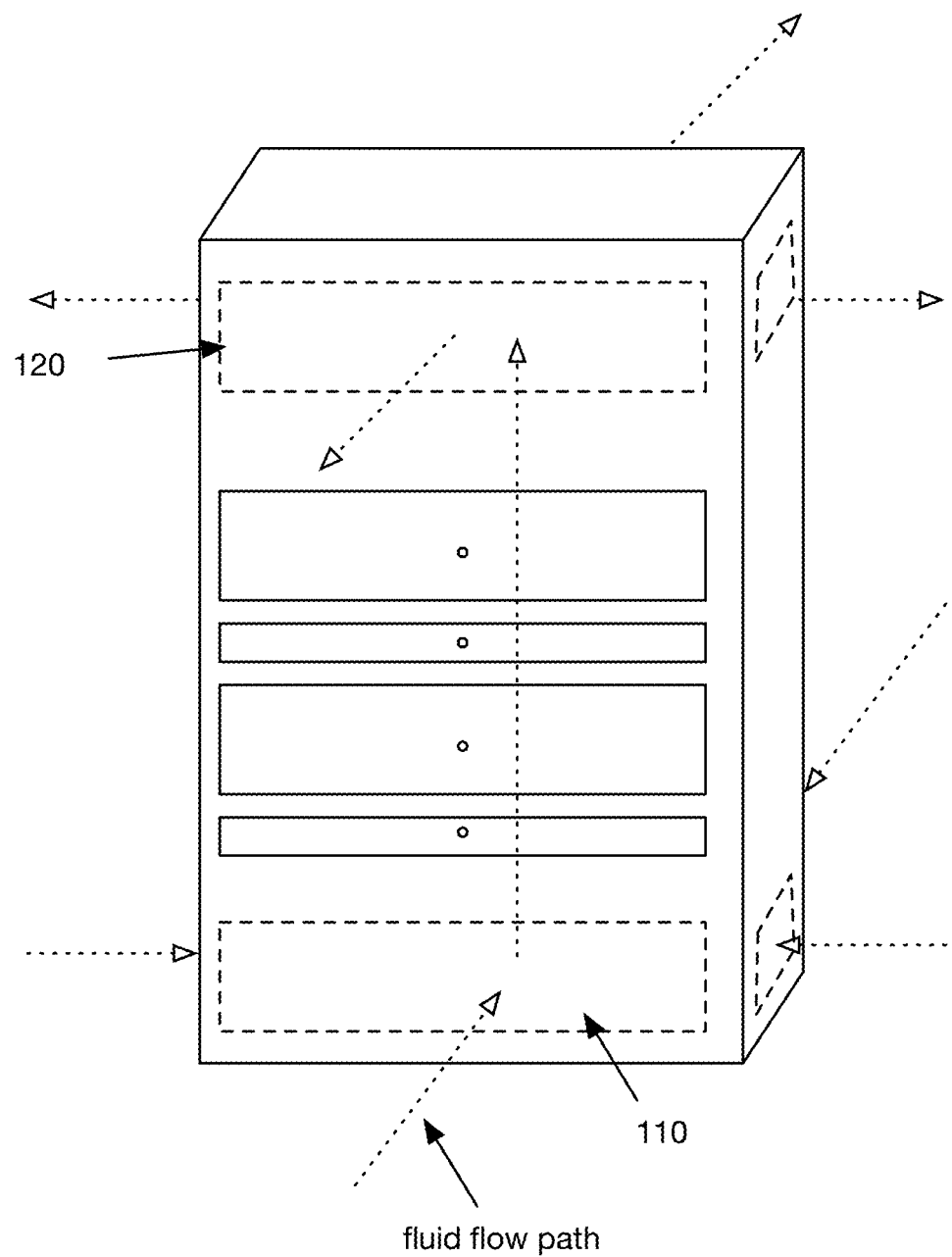
FIG. 8 is a schematic representation of fluid flow through an example of the system.

The outlet(s) 120 preferably functions to release (filtered) air into the environment and/or into an external system. The outlet(s) are preferably arranged proximal the active flow control mechanism, but the outlet(s) can be arranged distal the active flow control mechanism and/or with any suitable position relative to the active flow control mechanism. The outlet(s) are preferably proximal (e.g., near, within a target distance of, within a threshold distance of, closer to, etc.) a second end of the housing (e.g., on one or more broad faces of the housing having a surface normal perpendicular to the gravity vector, on one or more broad faces of the housing having a surface normal parallel to the gravity vector, etc.) where the second end opposes the first end, but the outlet can additionally or alternatively be arranged proximal the first end, proximal the center of the housing, and/or at any suitable location. In an illustrative example as shown in FIG. 14, the outlets are arranged proximal the top of the housing. The system preferably includes a single outlet, but can alternatively include multiple outlets (for example as shown in FIG. 8).

In variants, the inlet and/or outlet can be coupled to an external system. The inlet and/or outlet can be coupled by a manifold 190 (e.g., tubing, as shown for example in FIG. 13), can be designed to receive an output from the external system, and/or can be configured in any suitable manner. In a specific example, the inlet and/or outlet to the system can be coupled to the output of an HVAC system. However, the inlet and/or outlet can be coupled to a compressed air system, an air cylinder, an air curtain system, a fume hood, and/or to any suitable external system.

Figure 11:
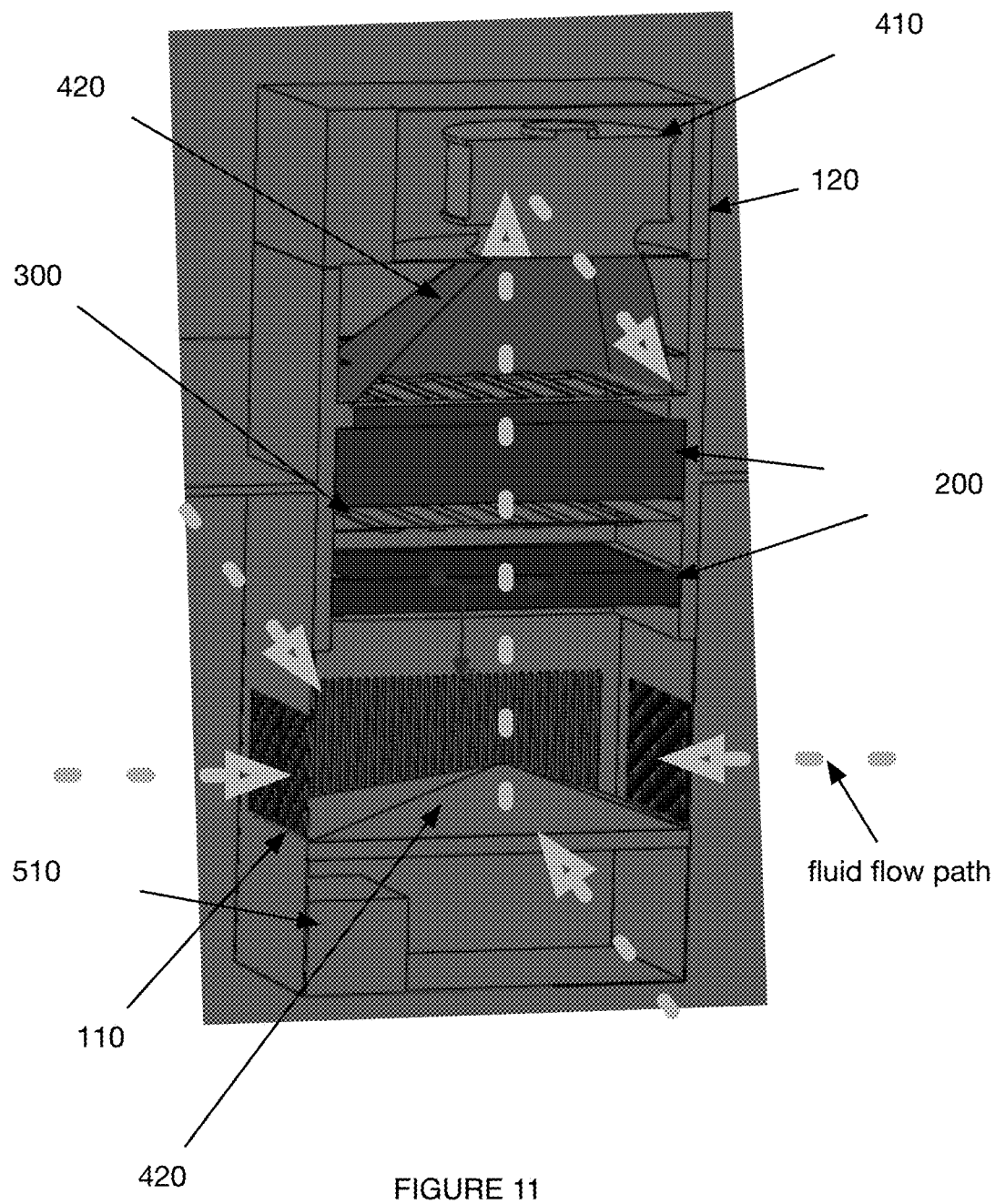
FIG. 11 is a schematic representation of an example of the system.

In variants as shown for example in FIG. 11, the inlet and/or outlet can include one or more (passive) flow control mechanisms. These flow control mechanisms can be used to promote and/or inhibit laminar flow of air entering the system. In examples, the flow control mechanisms integrated in the inlet and/or outlet can include: vents, fins, baffles, tortuous paths, one or more filters, aerodynamic plates (e.g., with three dimensional shape to direct fluid flow into or out of the housing such as pyramid, cones, etc.; configured to direct fluid along the fluid flow path; etc.), and/or any suitable features to induce desired fluid flow properties.

The outlet can direct the fluid flow up, down, left, right, in any suitable angle between 0° and 180° (e.g., where 0° corresponds to parallel to a longitudinal housing axis or gravity vector, and 180° corresponds to anti parallel to a longitudinal housing axis or gravity vector, where 0° corresponds to one edge of the outlet and 180° corresponds to an opposing edge of the outlet), straight out (e.g., parallel to a surface normal of a face of the housing), combinations thereof, and/or in any suitable direction. In a specific example, each outlet can include vents that can be configured to direct the fluid flow egress from the system. The orientation of the outlet vents can be changed to modify the fluid flow to be directed in any suitable direction out of the outlet.

Fluid expelled from the outlet preferably does not substantially disturb (e.g., change fluid currents by less than a threshold amount; changes fluid flow speed by less than 1%, 2%, 5%, 10%, 20%, etc. compared to when the system is shut down; changes fluid direction by less than 1°, 2°, 5°, 10°, 20°, etc. relative to when the system is shut down; changes the fluid turbulence within the environment by less than 1%, 2%, 5%, 10%, 20%, etc. compared to when the system is shut down; changes a Reynolds number for fluid within the environment by less than a threshold amount such as less than 1, 2, 4, 10, 20, 40, 100, 200, 400, 1000, etc.; changes a fluid velocity and/or direction by less than a threshold amount such as less than 0.01, 0.02, 0.04, 0.1, 0.2, 0.4, 1, 2, 4, 10 m/s, etc.; fluid exits the system with less than a threshold velocity such as less than 0.01, 0.02, 0.04, 0.1, 0.2, 0.4, 1, 2, 4, 10 m/s, etc.; etc.) the fluid flow in the environment proximal the system (e.g., the existing fluid flow within the environment; an air barrier formed by an air curtain proximal the system such as within a threshold distance of the air purification system, where an air curtain typically produces an air flow between about 30 and 40 cfm; etc.), but can disturb the fluid flow in the environment. For example, the fluid expelled from the outlet preferably does not interrupt or disturb (e.g., introduce turbulence into) laminar fluid flow within the environment proximal the system. In a second example, the fluid expelled from the outlet does not interrupt or disturb (e.g., pass through, break up, interfere with etc.) an air curtain proximal (e.g., within a threshold distance of, forming a threshold angle between the air flow into or out of the system and the system housing, etc.) the system.

The air purification system (e.g., an outlet and/or inlet thereof) is preferably arranged at least a threshold distance from objects (e.g., an air curtain, a person, a desk, a table, as shown for example in FIG. 3, etc.). The threshold distance is preferably between about 1 ft and 30 ft (e.g., 0.1 m, 0.5 m, 1 m, 2 m, 3 m, 5 m, 10 m, values therebetween etc.), but can be less than 1 ft or greater than 30 ft. In some embodiments, the threshold distance can define a zone proximal the system (e.g., where an external environment can be outside of the threshold distance). However, the zone can additionally or alternatively be defined based on the However, the air purification system can be less than the threshold distance (e.g., when the inlet and/or outlet is closed, when air flow directed in and/or out of the air purification system is directed at an angle relative to the object and the air purification system, etc.), and/or arranged in any suitable manner. In an illustrative example, an air purification system can be between about 1-30 feet from an air curtain (e.g., an air curtain surrounding a patient) where air expelled from the air purification system does not substantially penetrate the air barrier (e.g., cannot be perceived by a person within the air curtain, does not allow mixing between environments on either side of the air curtain, changes an air flow direction from the air curtain by less than a threshold angle such as 1°, etc.) formed by the air curtain. In a first variation of this example, the air flow vector from the system can be substantially perpendicular to the air barrier (e.g., directed straight on the air barrier, have an angle between 0-10°, etc.). In a second variation of this example, the air flow vector from the system (e.g., out of the outlet, into the inlet, etc.) can form an angle (e.g., a threshold angle such as 10-90°) relative to the air barrier (or other object(s) within the environment). However, the system can otherwise be arranged relative to other objects.

In a first example, the inlet can be upstream of the filter(s), the filter(s) can be upstream of the flow control mechanism, and the flow control mechanism can be upstream of the outlet. However, the components can be arranged within the housing in any suitable order (e.g., with respect to the fluid flow pathway, with respect to the fluid flow direction, etc.).

The housing preferably includes one or more access ports 150. The access ports function to enable user(s) to access one or more components of the system (e.g., to repair components, to replace a component, to install components, to reorient components, etc.). Access ports can be arranged on any suitable broad face(s) (and/or surface) of the housing. For example, the access port(s) can be arranged on the side, top, bottom, wrap-around to more than one side, and/or can be arranged at any suitable location. Each component can be associated with an access port. However, each access port can enable access to a plurality of components. Each access port is preferably electrically grounded (e.g., to the housing, to the ground, etc.; such as using a conductive wire). However, the access ports can be maintained at any suitable reference potential. In examples, the access port can include: a door, a panel, a cover, drawer, and/or any suitable access port can be used.

The housing can optionally include one or more handles 170 (e.g., to facilitate lifting and/or rearranging the system; such as arranged on one or more broad faces of the housing), housing translation system (e.g., to facilitate moving the system; such as wheels, treads, tracks, transportation mechanism, etc.), base (e.g., to facilitate reorientation of the system; such as configured to rotate the system in pitch, yaw, roll), weights (e.g., counterweights such as to decrease the risk of the housing tipping over), and/or any suitable elements.

The filter(s) 200 preferably function to remove (e.g., capture, destroy, degrade, etc.) one or more contaminants from the fluid within the lumen of the housing. Filters can remove contaminants: mechanically, chemically, photochemically, electrically, photoelectrochemically, thermally, biologically, and/or using any suitable mechanism. For example, an active filter (such as a PECO or other photocatalytic filter) can oxidize one or more contaminants by generating reactive radicals (e.g., hydroxyl radicals) to oxidize the contaminants. The filter (and/or the fluid filtration system) preferably does not produce ozone (e.g., produces less than a threshold amount of ozone such as 1 ppm, 100 ppb, 10 ppb, 1 ppb, 100 ppt, 10 ppt, 1 ppt, etc.), which can also act as a pollutant or contaminant (e.g., in indoor spaces). However, the filter (and/or air filtration system) can generate ozone and/or any reactive species. The system can include one or more filters of the same or different type. For example, the system can include 1, 2, 3, 4, 5, 6, 7, 8, 9, 10, 15, 20, values therebetween, and/or more than 20 filters. The filters are preferably removable (e.g., individually removable, collectively removeable), but can additionally or alternatively be permanently installed. The filter form factor is preferably matched to the form factor of the housing, but any suitable form factor can be chosen. In specific examples, the filter form factor can be polygonal (e.g., rectangular, square, etc.), cylindrical, spherical, hemispherical, and/or can be any suitable shape. The filter can be pleated and/or nonpleated. In examples, the filters can be planar, serpentine, honeycomb, fibrous, and/or have any suitable structure. The filter(s) can be single layer, multi-layer, coated, and/or otherwise be configured. In some embodiments, one or more filters can include one or more layers as disclosed in U.S. patent application Ser. No. 16/523,928, entitled "FLUID FILTRATION SYSTEM AND METHOD OF USE," and filed 26 Jul. 2019, which is incorporated herein in its entirety by this reference. In specific examples, the filters can include: mechanical filters or layers (e.g., HEPA filters; filters with any suitable MERV rating such as 8, 10, 12, 14, 16, 18, 20, etc.; etc.), photochemical (PC) filters or layers, photoelectrochemical (PEC) filters or layers, photoelectrochemical oxidation (PECO) filters or layers, contaminant-specific filters or layers (e.g., sorption filters such as a filter coated with a sorbent material such as activated carbon; SOX filters; NOX filters; VOC filters; etc.), anti-biologic filters or layers (e.g., antimicrobial, antifungal, antiviral, anti-peptidal, anti-nucleotide, etc.), electromagnetic filters or layers, and/or any suitable filters and/or layers can be used.

Anti-biologic filters function to remove biological contaminants from the contaminated fluid, but can additionally remove other contaminants. The anti-biologic filters can be specific (e.g., to particular classes of biological contaminants such as bacteria, viruses, gram-positive bacteria, gram-negative bacteria, eukaryotes, prokaryotes, fungi, etc.; to particular biological contaminants; etc.) or general. The anti-biologic filter can destroy, capture, deactivate, inhibit (or halt and/or prevent) growth, inhibit (or halt and/or prevent) reproduction of, kill, and/or otherwise remove contaminants from the fluid. The anti-biologic filter preferably includes an anti-biologic material, but can additionally or alternatively be structurally designed to and/or otherwise remove contaminants. The anti-biologic filter can be made of the anti-biologic material, (conformally or nonconformally) coated with the anti-biologic material, and/or otherwise incorporate anti-biologic material. Examples of anti-biologic materials include: graphene materials (e.g., fullerenes, graphite, graphene oxides, graphite oxides, etc.), two-dimensional materials (e.g., 2D molybdenum disulfide ($MoS_2$)), hydrogels (e.g., polycationic hydrogels such as chitosan derived hydrogels), polymer brushes (e.g., functionalized polymer brushes, brushes comprising bactericidal polymers, non-fouling polymer brushes, etc.), dendrimers, noble metals (e.g., copper, silver, gold, etc.), alloys (e.g., bronze, brass, copper-nickel-zinc, cupronickel, etc.), nanoparticles (e.g., silver nanoparticles, gold nanoparticles, etc.), photocatalytic materials, and/or any suitable anti-biologic materials can be used.

In an illustrative example, a photocatalytic filter can include a substrate (e.g., a fibrous substrate), photocatalytic material disposed on the substrate, support material (e.g., electrically conductive support material such as a metal, conductive polymer, etc.), and/or any suitable materials. The support material is preferably coupled to (e.g., in electrical contact with) the photocatalytic material, but the support material can be decoupled from the photocatalytic material. The photocatalytic material can be nanoparticulate (e.g., nanocrystals, nanoparticles, nanostructure, as disclosed in U.S. application Ser. No. 16/831,354 filed 26 Mar. 2020 entitled "SYSTEM AND METHOD FOR PHOTOELECTROCHEMICAL AIR PURIFICATION" incorporated in its entirety by this reference, etc.), mesoparticulate, microparticulate, macroparticulate, film (e.g., thin film), and/or have any morphology. Examples of photocatalytic material include: titanium dioxide (in anatase, rutile, and any other suitable phase), sodium tantalite, doped titanium dioxide, zinc oxide, inorganic carbonaceous materials (e.g., nanocarbon, graphene, carbon nanotubes, etc.), organic materials, and/or any other suitable substance(s) that catalyzes reactions in response to photon illumination. The photocatalytic material is preferably illuminated (e.g., directly illuminated) by the activation mechanism, but can be used without illuminating the photocatalytic material. In variants of this specific example, a photocatalytic filter can be used as a pre-filter, a primary filter, and/or perform any role as a filter for a fluid filtration system. In some variations of the photocatalytic filter (or a photocatalytic layer), the substrate can have a first MERV rating and the photocatalytic filter (or layer) can have a second MERV rating that is greater than the first MERV rating (e.g., conferred by disposing or coating the substrate with the photocatalytic material). For instance, the first MERV rating can be 8 and the second MERV rating can be 10. However, the second MERV rating can be less than or equal to the first MERV rating and/or the first and second MERV rating can be any suitable value. The second MERV rating can depend on the first MERV rating, the photocatalytic material (e.g., material composition, particle size, grain size, phase, etc.), the photocatalytic material loading (e.g., mass of loaded photocatalytic material, surface coverage fraction of the substrate with the photocatalytic material, etc.), the substrate (e.g., material composition, pore size, pore distribution, etc.), and/or any suitable properties.

In an illustrative example, an anti-biologic filter can include a substrate and photocatalytic material (e.g., PECO material, PEC material, PC material, etc.) deposited on the substrate. The photocatalytic material can exhibit anti-biologic function in the absence of illumination and/or with less than a threshold illumination typically expected to induce photocatalytic reactions. However, the photocatalytic material can exhibit anti-biologic function in the presence of illumination, when the illumination exceeds a threshold illumination (e.g., threshold photon flux, threshold intensity, etc.), and/or otherwise exhibit anti-biologic function. When an anti-biologic filter and photocatalytic filter are used in tandem, the filters can use the same or different photocatalytic materials.

Figure 7:
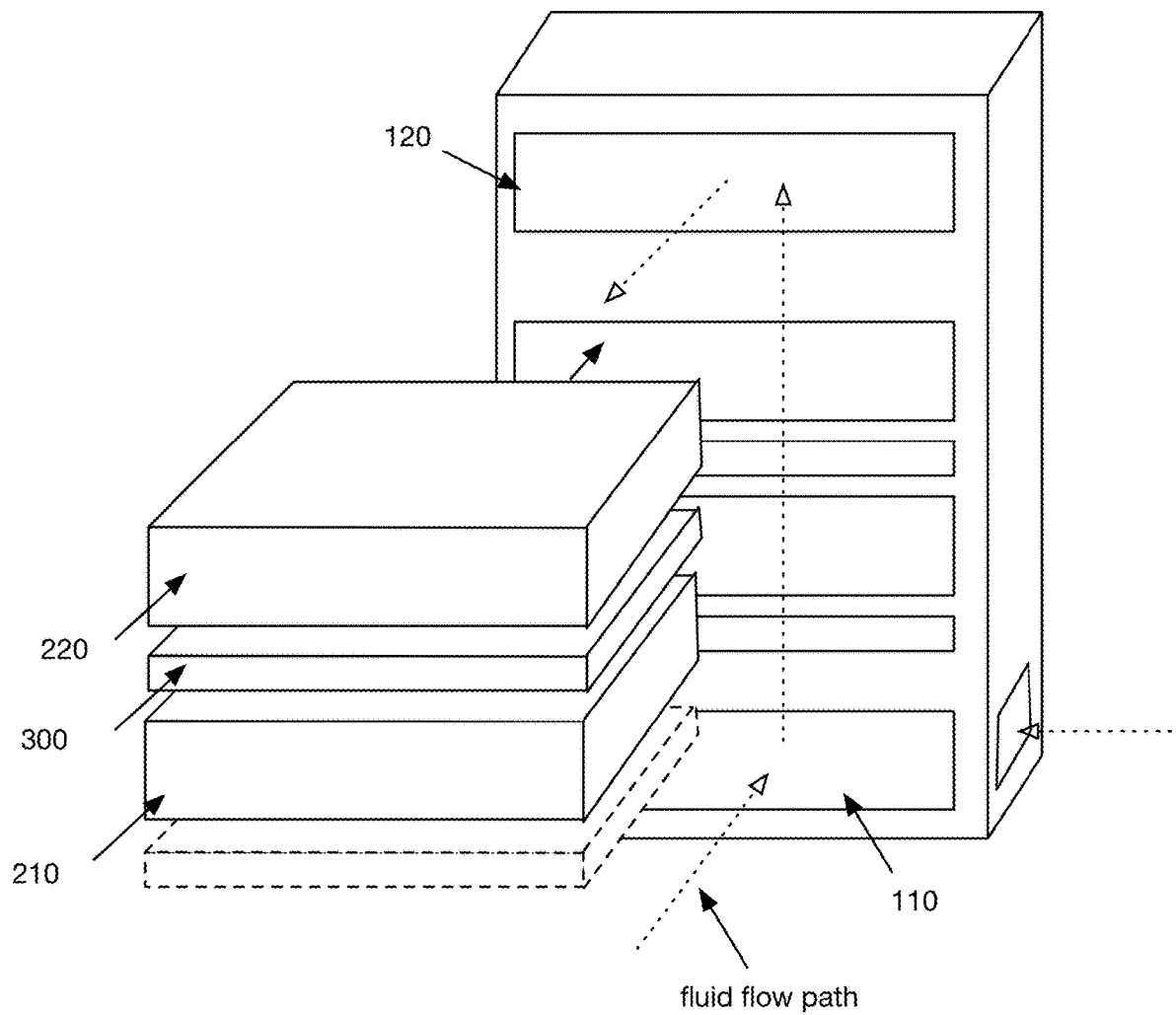
FIG. 7 is an exploded view of an example of the system.

In variants of the fluid filtration system including more than one filter, the filters can be arranged in any suitable order. In an illustrative example, a prefilter 210 (e.g., a mechanical filter, an anti-biologic filter, a sorbent filter, photocatalytic filter, etc.) can be arranged upstream (e.g., relative to a fluid flow vector) of a photocatalytic (e.g., PC, PEC, PECO, etc.) filter 220 (example shown in FIG. 7). However, the prefilter can be arranged downstream of the photocatalytic filter, the prefilter can be integrated into the photocatalytic filter, and/or the filters can be arranged in any suitable order.

In a first specific example of a fluid filtration system including more than one filter, the fluid filtration system can include a first photocatalytic filter 220a, a second photocatalytic filter 220b downstream of the first photocatalytic filter along the fluid flow path, and a third photocatalytic filter 220c downstream of the second photocatalytic filter along the fluid flow path. In this specific example, each photocatalytic filter can have an associated MERV rating. The MERV rating preferably increases from the first photocatalytic filter to the third photocatalytic filter, but the MERV ratings can be the same and/or decrease from the first photocatalytic filter to the third photocatalytic filter. For instance, the MERV rating for the first photocatalytic filter can be between about 6-10 (or values or ranges therewithin), the MERV rating for the second photocatalytic filter can be between about 8-14 (or values or ranges therewithin), and the MERV rating for the third photocatalytic filter can be between about 10-18 (or values or ranges therewithin). However, each filter can be associated with any suitable MERV rating. In this specific example, a first light source (e.g., set of light strips) can be arranged between the first and second photocatalytic filters and a second light source (e.g., set of light strips) can be arranged between the second and third photocatalytic filters. Each light source can include a set of light emitters (e.g., LEDs) configured to illuminate a surface of the filters proximal the light source. For instance, the first light source can include a set of light emitters directed toward the first photocatalytic filter and a second set of light emitters directed toward the second photocatalytic filter. In this specific example, the light sources (e.g., the first light source, the second light source, etc.) can be configured or operable to provide light with the same or different wavelengths. For instance, the first light source can provide visible radiation (e.g., with a wavelength or wavelength range between about 380 nm and 760 nm, between 400 to 700 nm, 400-450 nm, 400-500 nm, etc.; only visible radiation; etc.) and the second light source can provide ultraviolet radiation (e.g., with a wavelength or wavelength range between about 100 nm and 400 nm, UV-A radiation, UV-B radiation, UV-C radiation, only ultraviolet radiation or range therewithin, etc.). However, the first and second light source can additionally or alternatively provide both ultraviolet and visible radiation, and/or any suitable radiation. Surfaces of the photocatalytic filter that include (e.g., have disposed on them) photocatalytic material are preferably proximal the light source, but can be distal the light source and/or otherwise be arranged. Photocatalytic material can be disposed on an upstream surface (e.g., relative to a fluid flow pathway), downstream surface (e.g., relative to a fluid flow pathway), within a substrate (e.g., within pores and/or a three dimensional volume defined by the substrate), and/or otherwise be disposed on any suitable surface(s) of the first, second, and/or third photocatalytic layer. While the same light strip is preferably configured to illuminate each proximal filter (e.g., includes a set of light sources on both an upstream and downstream surface), each filter can be illuminated by separate light strips and/or otherwise be illuminated.

In variations of the first specific example, the fluid filtration system can include a multilayer filter 225. The multilayer filter is typically downstream of the third photocatalytic filter, but can be otherwise arranged within the system. The multilayer filter (or a layer thereof) preferably has a MERV rating between 12 and 16 (e.g., 12, 13, 14, 15, 16), but can have any suitable MERV rating (e.g., <12 such as 6, 8, 10; >16 such as 17, 18, 19, 20; etc.) or not have a MERV rating. The multilayer filter can include one or more of: a photocatalytic layer (e.g., a PECO filter activated by UV light, a PECO filter activated by visible light, a PECO filter activated by both UV and visible light, a PEC filter, etc.), a sorptive layer (e.g., activated carbon disposed on a substrate, on a scrim, between two or more scrims, between two or more substrates, etc.), a particle trapping layer, an electrostatic layer, a reactive layer, and/or any suitable layer(s). The sorptive layer is preferably the most upstream layer relative to the fluid flow pathway, but can be the most downstream layer, an intermediate layer, and/or otherwise be arranged. The photocatalytic layer is preferably the most downstream layer relative to the fluid flow pathway, but can be a most upstream layer, an intermediate layer (e.g., between two or more other layers), and/or can otherwise be arranged. Photocatalytic material of the photocatalytic layer is preferably electrically coupled to an electrically conductive material or layer (e.g., a metal mesh, a support layer, etc.), but be electrically isolated from the electrically conductive material and/or can otherwise be arranged. In these variations, the fluid filtration system can include a light source arranged to illuminate the multilayer filter (e.g., a photocatalytic layer thereof). The light source can be between the multilayer filter and a photocatalytic filter, be arranged before or after the set of filters, be arranged along a side or edge of one or more filters, and/or otherwise be arranged. For instance, a light strip can illuminate both the third photocatalytic filter and the multilayer filter (e.g., using a first set of light sources and a second set of light sources directed in different directions).

In a second variation (that can be combined with or separate from the first variation) of the first specific example, the different photocatalytic filters can have different photocatalytic efficiencies (e.g., degradation efficiencies, degree of oxidation of contaminants, single pass efficiency, multipass efficiency, degree of contaminant removal, etc.). For instance, each filter can degrade different contaminant species (e.g., based on a contaminant size, based on contaminant chemical properties, based on a contaminant identity, based on the photocatalyst, based on an excitation wavelength, etc.), can have different reaction efficiencies (e.g., based on different degrees of excitation, based on different excitation wavelengths, based on different loading, based on different photocatalytic materials, different exciton lifetimes, different free carrier lifetimes, different reactive species lifetimes, etc.), and/or can otherwise have different photocatalytic efficiencies. Typically, the photocatalytic efficiency increases from the first to the last (e.g., third) filter, but the photocatalytic efficiency can decrease, remain the same, and/or vary in any manner between the filters. For instance, the first photocatalytic filter can have an efficiency (e.g., single pass efficiency, average efficiency, efficiency when used in tandem with the other photocatalytic filters, efficiency when used in isolation, etc.) between about 10-50%, the second photocatalytic filter can have an efficiency between about 20-80%, and the third photocatalytic filter can have an efficiency between about 50%-100%. However, each filter can have any suitable efficiency.

In a second specific example of a fluid filtration system including more than one filter, the fluid filtration system can include a photocatalytic filter and a multilayer filter typically downstream (but potentially upstream) of the photocatalytic filter along the fluid flow path. The multilayer filter can include one or more of: a photocatalytic layer (e.g., a PECO filter activated by UV light, a PECO filter activated by visible light, a PECO filter activated by both UV light and visible light, etc.), a sorptive layer (e.g., activated carbon disposed on a substrate, on a scrim, between two or more scrims, between two or more substrates, etc.), a particle trapping layer, an electrostatic layer, a reactive layer, and/or any suitable layer(s). The sorptive layer is preferably the most upstream layer relative to the fluid flow pathway, but can be the most downstream layer, an intermediate layer, and/or otherwise be arranged. The photocatalytic layer is preferably the most downstream layer relative to the fluid flow pathway, but can be a most upstream layer, an intermediate layer (e.g., between two or more other layers), and/or can otherwise be arranged. In this specific example, a light source (e.g., set of light strips) can be arranged between the photocatalytic and multilayer filters and be configured to illuminate each filter. However, two or more light sources can be included to illuminate or excite the filters (e.g., a unique light source for each filter, shared light sources, etc.).

Variations of the second specific example can include a second photocatalytic filter. The second photocatalytic filter is preferably arranged between the photocatalytic filter and the multilayer filter, but can be upstream of the photocatalytic filter, downstream of the multilayer filter, or otherwise be arranged. In this variation, each photocatalytic filter can have an associated MERV rating. For instance, the MERV rating for the photocatalytic filter can be between about 6-14 (or values or ranges therewithin), the MERV rating for the second photocatalytic filter can be between about 8-16 (or values or ranges therewithin). However, each filter can be associated with or have any suitable MERV rating. These variations can include a second light source (e.g., set of light strips) that can be arranged between the photocatalytic filters, between the second photocatalytic filter and the multilayer filter, and/or otherwise be arranged.

In a second variation (that can be combined with or separate from the first variation) of the second specific example, the different photocatalytic and/or multilayer filters can have different photocatalytic efficiencies (e.g., degradation efficiencies, degree of oxidation of contaminants, single pass efficiency, multipass efficiency, degree of contaminant removal, etc.). For instance, each filter can degrade different contaminant species (e.g., based on a contaminant size, based on contaminant chemical properties, based on a contaminant identity, based on the photocatalyst, based on an excitation wavelength, etc.), can have different reaction efficiencies (e.g., based on different degrees of excitation, based on different excitation wavelengths, based on different loading, based on different photocatalytic materials, different exciton lifetimes, different free carrier lifetimes, different reactive species lifetimes, etc.), and/or can otherwise have different photocatalytic efficiencies. Typically, the photocatalytic efficiency increases from the first to the last filter along the air flow path, but the photocatalytic efficiency can decrease, remain the same, and/or vary in any manner between the filters. For instance, the photocatalytic filter can have an efficiency (e.g., single pass efficiency, average efficiency, etc.) between about 10-50% and the multilayer filter can have an efficiency (e.g., single pass, average efficiency, efficiency when used in tandem with the photocatalytic filter, efficiency when used in isolation, etc.) between about 50%-100%. However, each filter can have any suitable efficiency.

In a third specific example (which can be used in conjunction with the first and/or second examples) of a fluid filtration system including more than one filter, the fluid filtration system can include a first photocatalytic filter that is activated by (e.g., illuminated with) visible radiation and a second photocatalytic filter that is activated by (e.g., illuminated with) ultraviolet radiation. The first photocatalytic filter is typically upstream of the second photocatalytic filter relative to the air flow through the fluid filtration system, but can be downstream of the second photocatalytic filter. The first and second photocatalytic filter can include the same and/or different photocatalytic material(s).

The filter(s) are preferably arranged within the housing (e.g., retained within the lumen of the housing). The filter(s) are preferably arranged between the inlet and the outlet of the housing, but can be otherwise arranged. The filters are preferably secured to the housing using a filter retention mechanism 230. The filter retention mechanism can be part of (e.g., mounted to, manufactured into, etc.) the housing, part of the filter, distributed between the housing and the filter (e.g., filter can include a first portion that is complimentary to a second portion included in the housing), and/or be arranged in any suitable manner. In examples, the filter retention mechanism can include: adhesives, tracks, slots, groves, location fits, press fits, fasteners (e.g., screws, bolts, etc.), trays, compartments, and/or any suitable retention mechanism can be used.

The filter retention mechanism is preferably arranged such that when a filter is installed, the fluid flow path can only pass through the filter (e.g., preventing fluid flow around the filter within the housing). For example, the filter can divide the lumen into a first and second plenum (e.g., an inlet and outlet volume) where, during operation (and/or when the filter is secured), the fluid can pass between the first and second plenum through the filter. However, the filter (and/or filter retention mechanism) can be arranged such that the fluid flow can bypass the filter. In examples, the filter retention mechanism can include gasket(s), sealant(s), o-ring(s), tortuous pathway(s), fittings (e.g., parts machined to fit together within a target specification such as tolerance <0.001", <0.002", <0.005", etc.), and/or can include any suitable components to induce a desired fluid flow pathway. The resultant fluid seal (e.g., defined between the filter retention mechanism and housing, between the filter housing and system housing, etc.) preferably traces a perimeter of the filter or filter retention mechanism, but can additionally or alternatively extend along a face of the filter or be otherwise arranged.

The filter and/or filter retention mechanism are preferably symmetric (e.g., mirror symmetry, rotational symmetry, etc.) about a reference axis (e.g., such as an axis perpendicular to a gravity vector, an axis parallel to a gravity vector, an axis parallel to a face of the filter and/or filter retention mechanism, an axis perpendicular to a face of the filter and/or filter retention mechanism, etc.). This symmetry can enable a filter to be oriented with any suitable filter broad face upstream or downstream of the fluid flow. However, the filter and/or filter retention mechanism can be asymmetric (e.g., to enable installation of the filter within the housing in a single manner) and/or have any suitable symmetry.

Figure 10:
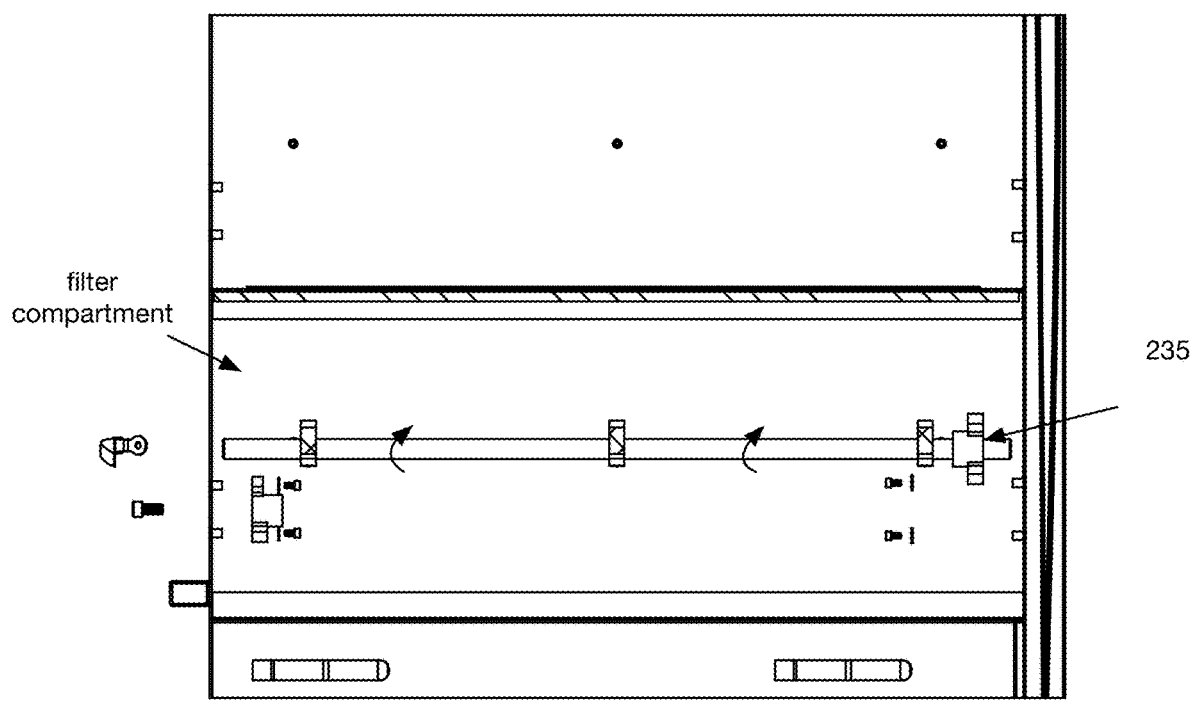
FIG. 10 is a side view of an example of a locking mechanism.

The filter retention mechanism optionally includes a locking mechanism 235. The locking mechanism functions to prevent the component from moving during operation and can ensure that the component is properly installed. The locking mechanism can function to prevent fluid flow from passing around the filter, can be used as an interlock (e.g., prevent one or more components from operating when the locking mechanism is disengaged), and/or can be used in any suitable manner. In examples, the locking mechanism can include: interference fit (e.g., friction fit between filter and filter retention mechanism), pressure mechanisms (e.g., one or more springs configured to apply a spring force against the filter such as to compress a gasket, a lobed cam that biases the filter against a housing ledge or gasket, example shown in FIG. 10, etc.), latch-and-tool (e.g., keys, specially designed tools 240, etc. that engage one or more holder such as plungers, dowels, etc. to hold the filter in the filter retention mechanism), adhesive (e.g., cured adhesive such as epoxy), and/or any suitable locking mechanism can be used. In an illustrative example, a cam mechanism can raise (and/or lower) a filter (e.g., with or without raising a filter track) to press against (e.g., compress) a gasket (or filter).

In one variation, the filter retention mechanism is a cam (and follower) mechanism, including a cam mounted to a shaft. The cam mechanism preferably biases a filter (e.g., the filter edges, a filter frame, etc.) toward a gasket or ledge along the housing (e.g., filter cavity), wherein the bias force forms a fluid seal between the filter and housing. The cam mechanisms are preferably arranged below the filter cavity, and bias the filter upward, but can additionally or alternatively be arranged above the filter cavity, and bias the filter downward. The system preferably includes two cam mechanisms (e.g., a left and right mechanism), but can additionally or alternatively include one, three, or any other suitable number of cam mechanisms. The cam mechanisms are preferably arranged with the shaft extending along a depth (e.g., front-to-back) axis of the housing (e.g., parallel the filter insertion axis, parallel a filter insertion broad face), but can be arranged along a lateral axis or along any other suitable axis. The shaft is preferably statically mounted to one or more cams, and rotates the cam along a shaft rotation axis, but the shaft can be otherwise mounted to the cam or rotate the cam. The cam(s) are preferably mounted to the shaft ends, but can additionally or alternatively be evenly or unevenly distributed along the shaft length. The cam lobes can be symmetric, asymmetric, and/or have any suitable symmetry. In variants, the cam lobes can be egg-shaped, oval, spiral (e.g., a single turn of a spiral such that the lobe includes a lip), and/or can have any suitable shape.

In operation, the cam mechanism can be rotated in one direction (e.g., clockwise or counterclockwise) to raise (and/or lower) a filter tray to engage the locking mechanism and rotated in the opposite direction (e.g., counterclockwise or clockwise) to disengage the locking mechanism. The cam lobes preferably actuate the filter (tray) symmetrically (e.g., maintain the orientation of a side and/or edge of the filter with respect to the gravity vector) but can actuate the filter (tray) asymmetrically. However, additionally or alternatively, the rotation mechanism can be rotated by a predetermined amount (e.g., 45°, 60°, 90°, 180°, 360°, etc.) in any direction (e.g., clockwise and/or counterclockwise) to engage the locking mechanism and can be rotated by a second predetermined amount (e.g., the same and/or different from the first predetermined amount in the same and/or different direction) to disengage the locking mechanism and/or the cam mechanism can be operated in any suitable manner. The cam mechanism can be actuated using a tool (e.g., a key, custom tool, hex key, knob, etc.), be manually actuated, or otherwise actuated.

In an illustrative example of the locking mechanism in use, the locking mechanism can be engaged during the operation of the system. When the locking mechanism is not engaged, an optional interlock (e.g., sensor) can be tripped (disengaged) such that the system cannot operate. The interlock can be located on the filter, on the locking mechanism, on the filter retention mechanism, on the housing, and/or arranged in any suitable manner. In a specific variant of this example, the interlock can include a (displacement) sensor arranged on the housing (e.g., along a lip of the filter cavity). When the filter is installed (e.g., locking mechanism engaged, filter inserted into the housing, etc.), the sensor can be engaged enabling the system to operate (e.g., enabling power to reach the flow control module, the activation mechanism, etc.; transmitting a signal enabling operation of the system; etc.).

The filter(s) can optionally include a filter identifier. The filter identifier can be a unique identifier (e.g., to identify the specific filter such as date of manufacture, location of manufacture, lot number, etc.), a common identifier (e.g., for same type of filter, filter manufactured in specific manner, etc.), and/or any suitable filter identifier can be used. For example, the filter identifier can include an NFC chip, beacon (e.g., Bluetooth beacon), RFID, barcodes, and/or any suitable identifier can be used. In variants, the system can initiate operation in response to filter identifier verification (e.g., by the system, remote management system, etc.), log filter use, and/or otherwise use filter identifier information.

The system can optionally include one or more activation mechanisms 300. The activation mechanisms can function to emit any suitable energy (e.g., light, heat, electricity, etc.) to activate (and/or prime) filter(s) and/or remove (e.g., degrade, destroy, etc.) contaminant(s). The activation mechanisms can be configured to emit energy directionally and/or non-directionally. The activation mechanisms can directly or indirectly activate the filter (and/or layers or materials thereof). Examples of activation mechanisms include: chemical activation mechanisms (e.g., desiccants, catalysts, reducing agents, oxidizing agents, etc.). optical activation mechanisms (e.g., light sources), electrical activation mechanisms, thermal activation mechanisms (e.g., radiative, conductive, convective heat sources; heat sinks; etc.), and/or any suitable activation mechanisms. The activation mechanisms preferably provide at least a threshold amount of energy or a threshold energy density to the filter, but can provide less than a threshold amount of energy or energy density, a predetermined energy or energy density, and/or any suitable amount of energy and/or energy density to the filter(s). The amount of energy provided can be controlled by: a distance between the activation mechanism (or sources thereof) and the filter (e.g., defined by a structural offset between the filter and activation mechanism; automatically adjusted based on filter loading, age, or other parameters, etc.), an operation setting of the activation mechanism (e.g., a power supplied to the activation mechanism, a temperature of the activation mechanism, etc.), and/or otherwise be controlled.

The activation mechanisms can be arranged upstream or downstream of the filter(s) relative to the fluid flow path. However, additionally or alternatively, the activation mechanisms can partially or fully surround the filter, be adjacent to the filter, be integrated into the filter, and/or be arranged at any suitable location. When the activation mechanism is arranged between two (or more filters), the activation mechanism can be equidistant between the filters and/or closer to one or more filters. In an illustrative example as shown in FIG. 140, the activation mechanism can be separated from a photocatalytic filter by a first distance 350 and separated from a prefilter by a second distance 360 where the first distance is less than the second distance. In a second example, a photocatalytic prefilter is separated from an activation mechanism by a first separation distance and a multilayer filter is separated from the activation mechanism by a second distance. However, the first distance can be equal to or greater than the second distance.

The activation mechanism is preferably arranged perpendicular to the fluid flow direction (e.g., a surface normal to a broad face of the activation mechanism is arranged parallel to the fluid flow direction), but the activation mechanism can be parallel to the fluid flow direction, intersect the fluid flow direction at any suitable angle (e.g., wherein the fluid flows through the activation mechanism), not intersect the fluid flow, and/or the activation mechanism can have any suitable arrangement relative to the fluid flow direction. The activation mechanism is preferably configured to (e.g., defines or includes one or more holes, gaps, leakages, spaces, etc.) enable the fluid flow to pass through (e.g., next to, along, etc.) the activation mechanism. However, additionally or alternatively, the activation mechanism can be sealed (e.g., configured to require the fluid flow path to follow a bypass pathway, release less than a threshold amount of VOCs, etc.), define a flow path therethrough (e.g., through the thickness, through the width, etc.), and/or can be arranged in any suitable manner. The activation mechanism is preferably planar, but can alternatively be curved (e.g., arcuate), cylindrical, and/or have other geometry. The activation mechanism(s) are preferably retained in the housing using activation mechanism retention mechanisms. The activation mechanism retention mechanisms can be the same as and/or different from the filter retention mechanisms. However, the activation mechanism(s) can be retained by the filter retention mechanism, integrated into the housing, and/or arranged in any suitable manner.

Figure 15:
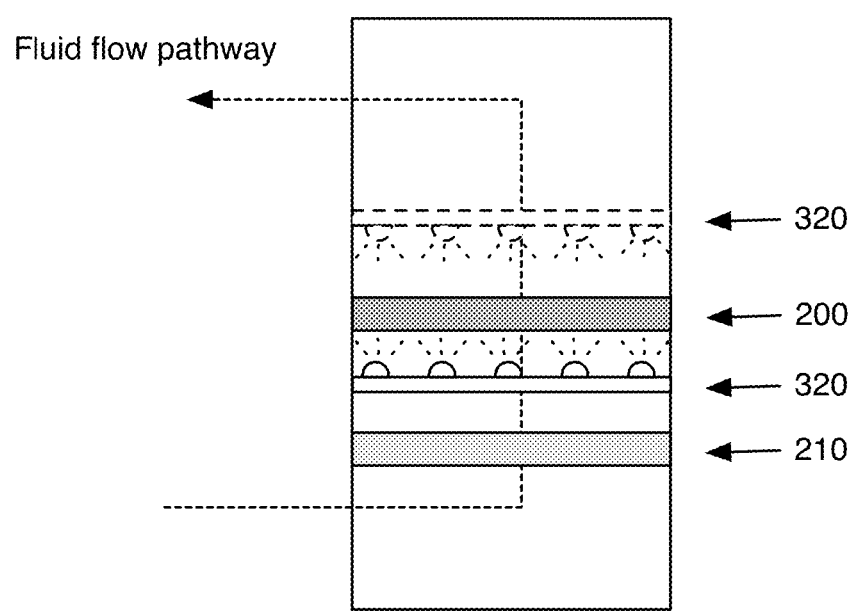
FIG. 15 is a schematic representation of an example of directly illuminating a filter.
Figure 16:
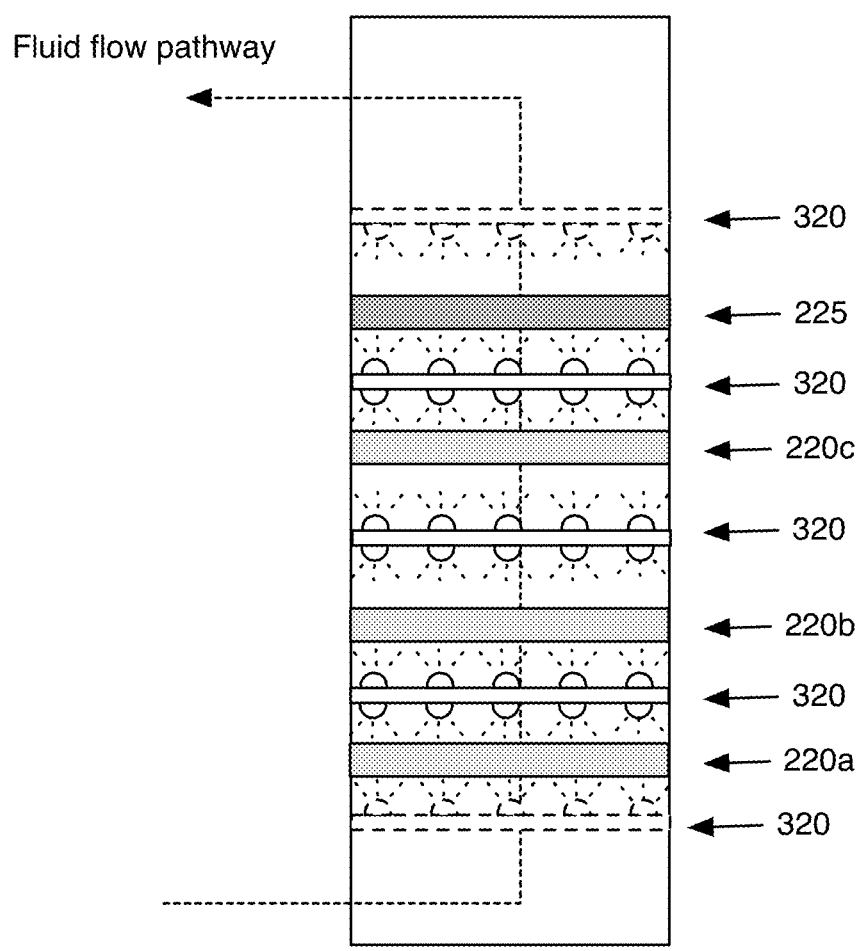
FIG. 16 is a schematic representation of an exemplary embodiment of an air purification system.

The activation mechanism can include one or more sources 310. Each source can be configured to emit the same and/or different energy (e.g., type, wavelength, intensity, etc.). In a specific example, the activation mechanism can include a rectangular grid of sources wherein each source is separate from neighboring sources by a lateral distance (e.g., 0.1 in, 0.5 in, 1 in, 2 in, 5 in, etc.) and a longitudinal distance (e.g., 0.1 in, 0.5 in, 1 inch, 2 inches, 5 inches, etc.; the same or different from the lateral distance). However, the sources can be arranged on a curvilinear grid, radial grid, randomly, and/or have any suitable arrangement. Each source can be a point source, linear source, areal source, and/or have any suitable geometry. All of the sources are preferably constrained to a plane (e.g., a plane normal to a broad face of the filter, a plane normal to the gravity vector, a plane parallel to a suitable broad face of the housing, etc.), but one or more of the sources can be arranged in any orientation in 3D space. All of the sources are preferably arranged on the same side of the activation mechanism. However, one or more sources can be arranged on different sides of the activation mechanism (e.g., be directed in different directions), and/or be arranged in any suitable manner. In an illustrative example as shown in FIG. 15, the sources can be arranged on a first side (e.g., broad face) of the activation mechanism, where the first side is proximal a primary filter (e.g., a photocatalytic filter, a PECO filter, a mechanical filter, a sorptive filter, an anti-biologic filter, etc.). However, the first side can be distal the primary filter, the activation mechanism can include sources on two or more sides, the first side can be proximal a prefilter, and/or the sources can be arranged on any suitable side of the activation mechanism. In a specific example, the activation mechanism can include a set of light strips 320 (e.g., 1, 2, 3, 4, 5, 10, 20, 30, 40, 50, 100, etc. strips), wherein each light strip includes a set of sources (e.g., 1, 2, 3, 4, 5, 6, 10, 20, 30, 50, 100, etc. sources). The set of light strips are preferably separated from one another by a gap 330 (e.g., to enable fluid to flow through the activation mechanism). The set of light strips are preferably substantially parallel to one another (e.g., nonintersecting, arranged laterally, arranged longitudinally, arranged on a common plane, etc.), but can be arranged at an angle, zigzag, serpentine, intersecting, arranged on different planes (e.g., planes arranged parallel or perpendicular to a gravity vector, planes arranged parallel or perpendicular to a vector parallel to a longitudinal or lateral vector of the housing, etc.), and/or can have any suitable orientation. However, the light stripes can be sources (e.g., linear sources), and/or the activation mechanism can include any suitable structure.

Figure 6:
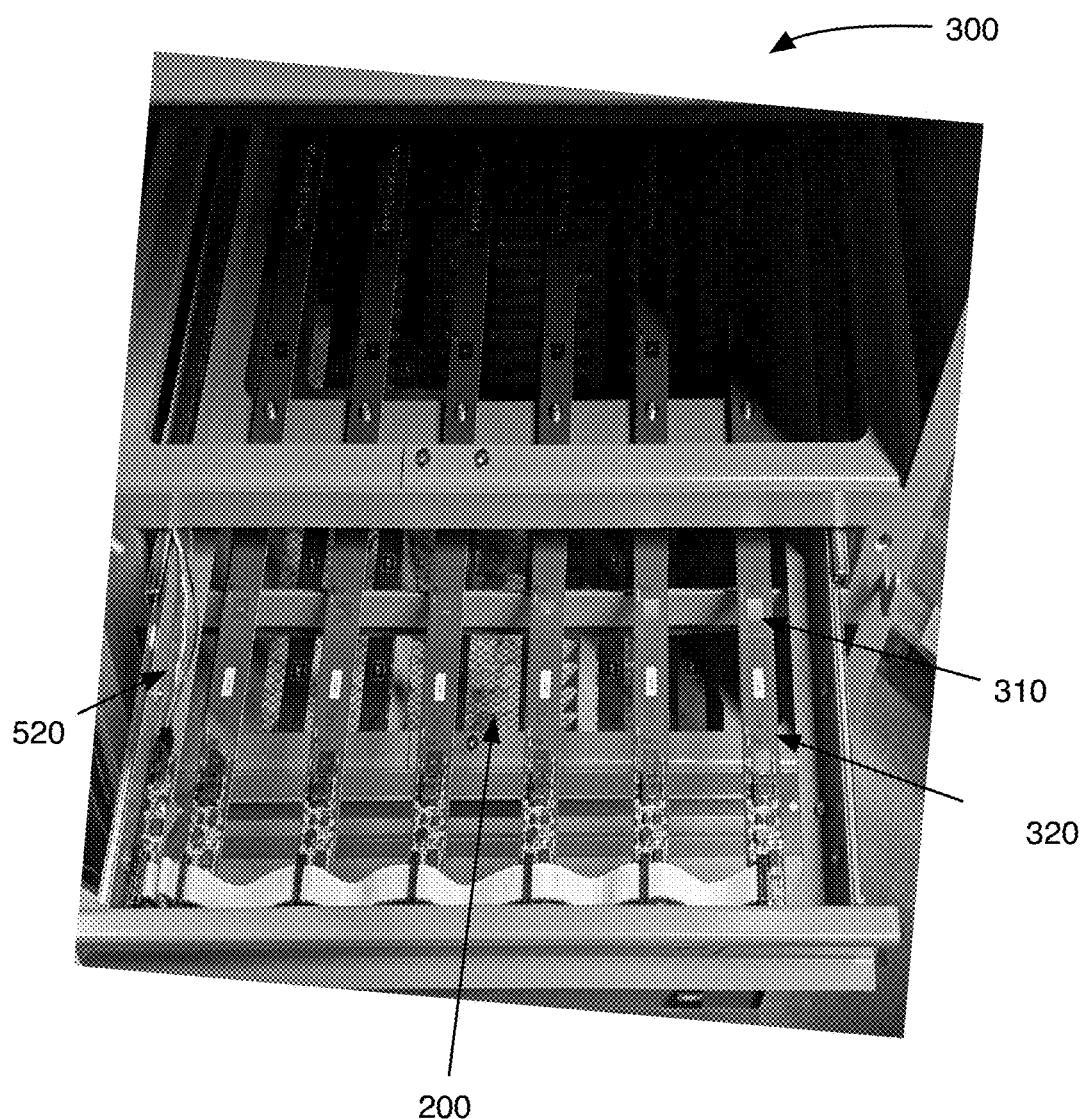
FIG. 6 is a schematic representation of an example of a filter and an activation mechanism.

In an illustrative example, when the system includes a photocatalytic filter, the activation mechanism can include one or more light sources. Examples of light sources include: incandescent sources, light emitting diodes, lasers, sunlight, fluorescent lamps, gas discharge lamps, phosphors, nonlinear sources, and/or any suitable light source(s). The light sources are preferably configured to emit light that is absorbed by the photocatalytic filter (e.g., by nanostructures, nanoparticles, etc. of the photocatalytic filter). However, the light source can additionally or alternatively be configured to emit light that is ultraviolet (e.g., any suitable wavelength and/or range thereof between 100-400 nm such as 315-400 nm, 280-315 nm, 100-280 nm, etc.), visible (e.g., any suitable wavelength and/or range thereof between 400-800 nm such as 400-450 nm, 400-500 nm, etc.), infrared (e.g., any suitable wavelength and/or range thereof between 800 nm-1 mm such as 800-1000 nm, 1-2 µm, 2-20 µm, etc.), light that is absorbed by one or more contaminant (e.g., electronic resonance, vibrational resonance, rotational resonance, combinations thereof, etc.), combinations thereof, and/or any suitable light. The light source(s) preferably (e.g., in isolation, in tandem, cooperatively, etc.) illuminate the photocatalytic filter with at least a threshold illumination (e.g., a threshold photon flux, a threshold intensity, a threshold irradiance, etc.), but can illuminate the photocatalytic filter with less than the threshold illumination, a predetermined illumination intensity, and/or with any suitable illumination. The threshold irradiance can be 0.1 W/m$^2$, 0.5 W/m$^2$, 1 W/m$^2$, 5 W/m$^2$, 10 W/m$^2$, 20 W/m$^2$, 25 W/m$^2$, 30 W/m$^2$, 50 W/m$^2$, 100 W/m$^2$, 200 W/m$^2$, 1000 W/m$^2$, less than 0.1 W/m$^2$, greater than 1000 W/m$^2$, and/or any suitable threshold irradiance. In a variant of this example as shown in FIG. 6, the light source can be arranged above the photocatalytic filter. In this variant, the light source can be arranged to illuminate the photocatalytic filter. In this variant, the light source can be removed from the housing, inverted, and reinstalled in the housing (for example to illuminate a second filter arranged above the light source). In a second variant of this example, when the system includes a prefilter, the light sources can directly illuminate the photocatalytic filter and not directly illuminate (e.g., not illuminate, illuminate through reflections, illuminate via scattering from other surfaces within the system, illuminate with less than a threshold irradiance, etc.) the prefilter. For instance, the light sources can be arranged to illuminate (e.g., facing) the photocatalytic filter and not face the prefilter. However, the light source and filter(s) can be arranged in any suitable manner.

Figure 9:
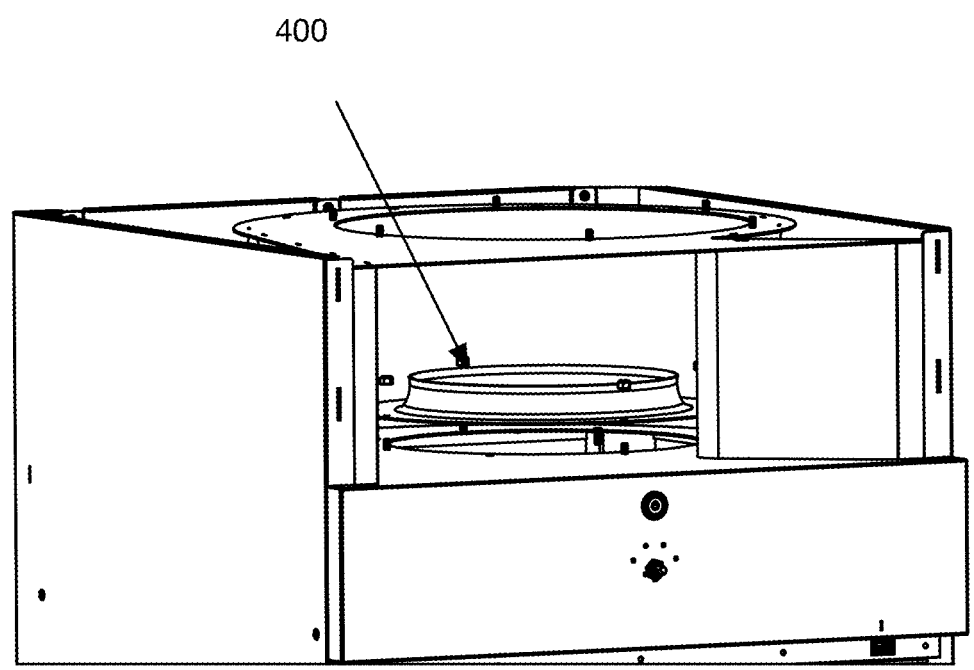
FIG. 9 is a schematic representation of an example of fan placement within the system.

Flow control mechanism 400 can function to bring (e.g., impel) fluid into the system (e.g., into the housing) and/or expel fluid out of the system (e.g., out of the housing). The flow control mechanism is preferably mounted in the housing (e.g., proximal the top of the housing, proximal the bottom of the housing, example as shown in FIG. 9, etc.). The flow control mechanism is preferably proximal the outlet, but can be proximal the inlet, distal the outlet, distal the inlet, and/or arranged in any suitable location. The flow control mechanism is preferably arranged downstream (e.g., relative to the fluid flow vector) of the filter(s). Having the flow control mechanism downstream of the filters can function to remove contaminants from the air before the air interacts with the flow control mechanism. However, one of more filters can be downstream of the flow control mechanism. The flow control mechanism can include active flow control mechanisms, passive flow control mechanisms, and/or any other suitable flow control mechanisms. However, any suitable flow control mechanisms can be included.

The active flow control mechanisms 410 preferably function to urge air to flow through the system (e.g., from the inlet to the outlet). Examples of active flow control mechanisms include: impellers, fans, propellers, jets, rotors, reciprocating pumps, centrifugal pumps, and/or any suitable mechanism for urging fluid flow. However, the active flow control mechanism can be supplied by an external system (e.g., an HVAC system), and/or any suitable flow control mechanism can be used.

The passive flow control mechanisms 420 can function to modify characteristics of the fluid flow (e.g., turbulence, speed, path, temperature, pressure, etc.). Examples of passive flow control mechanisms can include: baffles, vents, seals, gaskets, hoses, tubing, chambers (e.g., open spaces within the housing), and/or any suitable structure(s) to modify the fluid flow to a desired fluid flow.

The power supply 500 preferably functions to provide power (e.g., electricity) to other components (e.g., flow control mechanism, activation mechanisms, sensors, etc.). The power supply can be configured to provide alternating current (AC) power and/or direct current (DC) power. The power supply is preferably an integrated unit, but can be distributed (e.g., a separate power supply can supply power to one or more components). The power supply is preferably powered by (e.g., connected to) the mains electrical lines. However, the power supply can additionally or alternatively be solar powered, wind powered, thermoelectric, piezoelectric, and/or powered in any suitable manner. The power supply preferably includes one or more power storage components (e.g., capacitors, batteries, etc.) that can function to provide back-up power (e.g., when the primary source of power is not available).

The power supply is preferably mounted in the housing, but the power supply can be outside the housing (e.g., in a separate housing and/or unit) and/or arranged in any suitable location. The power supply can be mounted proximal the bottom, proximal the top, along one or more sides, arranged within the lumen, and/or mounted at any suitable location within the housing. In some examples, the power supply is arranged proximal the inlet (e.g., so that any VOCs released from the power supply can be filtered by the filter(s)). However, the power supply can be arranged at any suitable location relative to the inlet or housing.

Figure 4C:
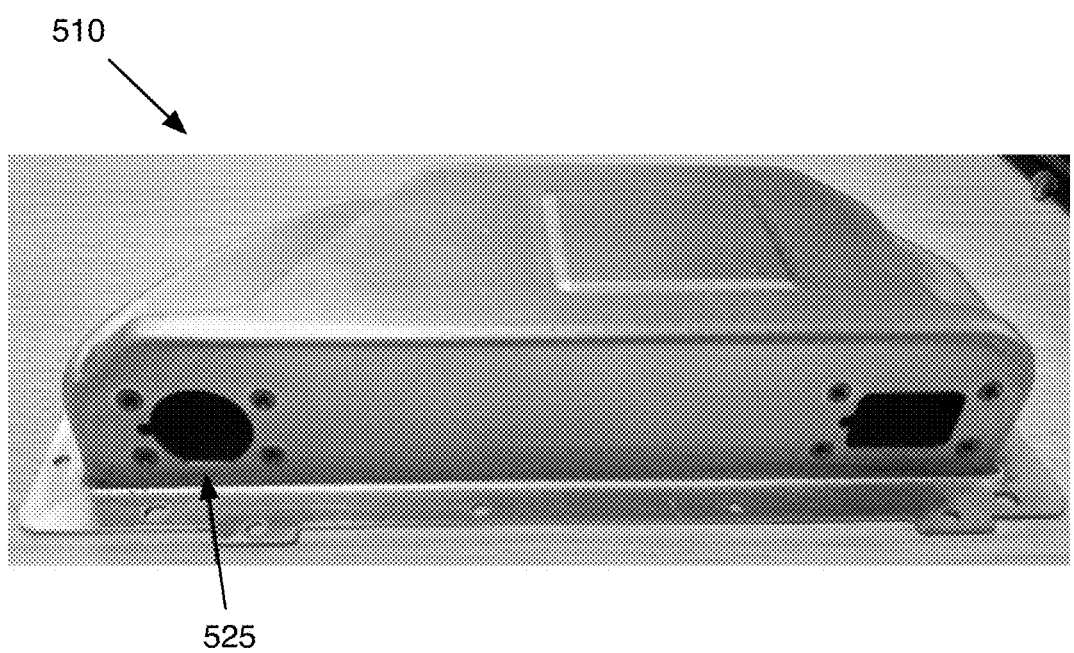

In some embodiments, the power supply can be environmentally isolated from the lumen (and/or the environment within the region where the system is housed) by a power supply housing 510. In these embodiments, environmentally isolating (e.g., fluidly isolating) the power supply can prevent (and/or minimize such as reduce to below a target threshold) the release of VOCs produced during manufacture and/or operation of the power supply (e.g., due to outgassing, due to oxygen ionization, etc.) from entering the environment (and/or contaminating the filters). In a specific example, as shown in FIGS. 4A, 4B, and 4C, the power supply housing 510 is preferably a metal enclosure, but can additionally or alternatively be made of plastic, ceramic, or made of any other suitable material. The power supply housing preferably forms a fluid-impermeable seal around the power supply, but can form any other suitable seal. The power supply housing can include gaskets, seals, filters, sealants 530, and/or any other suitable mechanism to prevent a release of a threshold amount of VOCs (e.g., a threshold percentage of VOCs produced and/or present in or near the power supply such as 10%, 25%, 33%, 50%, 75%, 90%, 95%, 97%, 99%, 99.9%, 99.99%, 99.998%, 99.999%, 100%, etc.; a threshold mass of VOCs such as 1 ng, 10 ng, 100 ng, 1 µg, 10 µg, 100 µg, 1 mg, 10 mg, 100 mg, 1000 mg, etc.; a threshold volume of VOCs such as 1-100 fL, 1-100 pL, 1-100 nL, 1 µL, etc.; a threshold rate of VOC release such as 0.001, 0.01, 0.1, 1, 10, 100 µg/m$^2$/s, 0.001, 0.01, 0.1, 1, 10, 100 g/m$^2$/s, etc.; etc.) out of the power supply housing (e.g., by trapping, reacting with, etc. the VOCs). In a first variant, the power supply housing can fluidly seal the power supply from the housing interior (e.g., the lumen). In a second variant, the power supply housing can fluidly seal the power supply environment from the outside environment. However, the power supply housing can fluidly seal the power supply (and/or its associated environment) from any suitable environment. In these embodiments, the sealed power supply can use the power supply housing as a heatsink (e.g., wherein waste heat is dissipated into the ambient environment), can include a cooling system (e.g., with coolant flowing therethrough), and/or be otherwise cooled. Wire ports defined in the power supply housing are preferably fluidly sealed (e.g., with epoxy, a gasket, sealant, etc.), but can additionally or alternatively remain open.

The power supply is preferably electrically coupled to the components via wires 520, but the power supply can be coupled to one or more components wirelessly (e.g., via induction). In variants, the wires are preferably contained in a wire compartment 525, but can be loose, and/or can be arranged in any suitable manner. The wire compartment (and/or free wires) is preferably arranged along a corner of the housing (e.g., a corner proximal the power supply, proximal an electrical outlet in the housing, extending along a housing height, etc.). However, the wire compartment (and/or wires) can be along a side of the housing and/or arranged in any suitable manner within the housing. The wire compartment preferably includes wire outlets at positions along the housing to supply power to one or more component. In a specific example, wires can extend out from the wire compartment substantially parallel to the activation mechanism to provide couple the activation mechanism to the power supply. In a second specific example, the trays retaining the activation mechanism can include electrical contacts (e.g., powered rails), or include wiring extending therethrough. However, the activation mechanism can be directly (e.g., via wires) and/or indirectly (e.g., wirelessly) connected to the wire compartment and/or power supply. However, the wire compartment can be configured in any suitable manner.

The system can optionally include one or more sensors 600, which function to detect one or more parameters of operation of the system. Sensors can additionally and/or alternatively function to provide feedback (e.g., for an active feedback loop, for a passive feedback loop, etc.) and/or control the operation of one or more system components. Sensors can be mounted at any suitable location within the housing (e.g., proximal the inlet, proximal the outlet, adjacent to one or more filters, adjacent to the power supply, adjacent to the flow control mechanism, etc.). Examples of sensors can include: displacement sensors (e.g., contact type such as switches, buttons, magnetic sensors, etc.; non-contact type such as optical, ultrasound, eddy current, etc.; etc.), fluid flow sensors (e.g., speed, direction, etc.), pressure sensors (e.g., air pressure), humidity sensors, temperature sensors, contaminant sensors (e.g., quantity, identity, etc.), loading sensors (e.g., filter orientation, activation mechanism orientation, locking mechanism engaged state, etc.), time sensors (e.g., filter lifetime, filter use time, system operation time, activation mechanism operation time, etc.), and/or any suitable sensors can be included.

In a specific example of using a sensor for feedback and/or system control, when a sensor detects that the system is open (and/or that a filter is not installed, is installed incorrectly, etc.), power can be shut off to the flow control mechanism, to the activation mechanism, and/or to any suitable component. However, the sensor readings can be used in any suitable manner.

The system can optionally include a user interface 700, which functions to provide information to the user and/or enables the user to input one or more operation settings to the system. Operation settings can include: operation mode (e.g., quiet, high throughput, etc.), noise level, rate of fluid throughput, volume of fluid turnover, flow rate, impeller speed, activation energy (e.g., intensity, wavelength, etc. of the activation mechanism), power draw, contaminants filtered, and/or any suitable settings can be controlled. The user interface is preferably arranged along the front of the housing (e.g., on broad face) on the side of the broad face not in contact with the lumen. However, additionally or alternatively, the user interface can be arranged along the front of the housing on the side of the broad face in contact with the lumen), on any side and/or face of the housing (e.g., in contact with the lumen, not in contact with the lumen), wireless (e.g., an application that runs on a user device, an application that runs on dedicated hardware, etc.), and/or can be arranged in any suitable location. In examples, the user interface can include: a display, a touchscreen, mechanical actuators (e.g., knobs, switches, buttons, etc.), sliders, hands-free (e.g., voice controlled, holographic, gesture based, etc.), and/or any suitable user interface can be used.

Figure 12A:
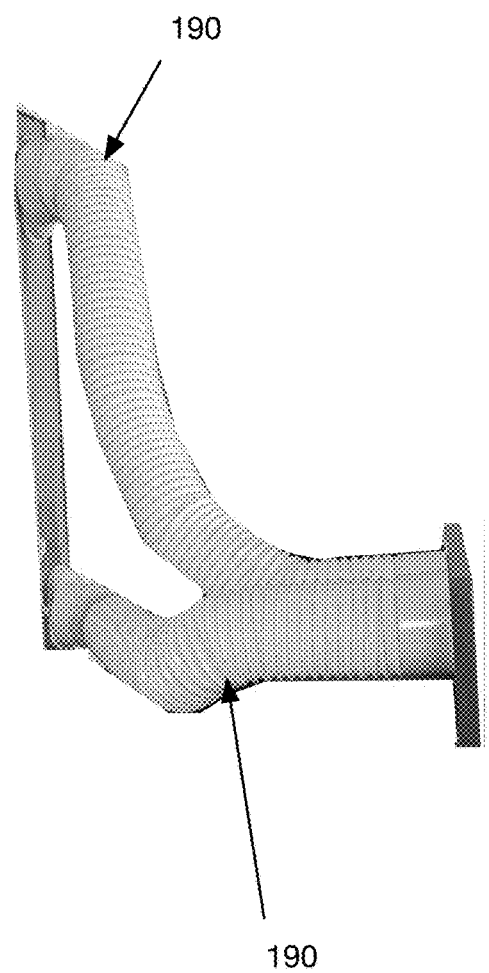
FIGS. 12A and 12B are illustrative examples of a fluid manifold set.
Figure 12B:
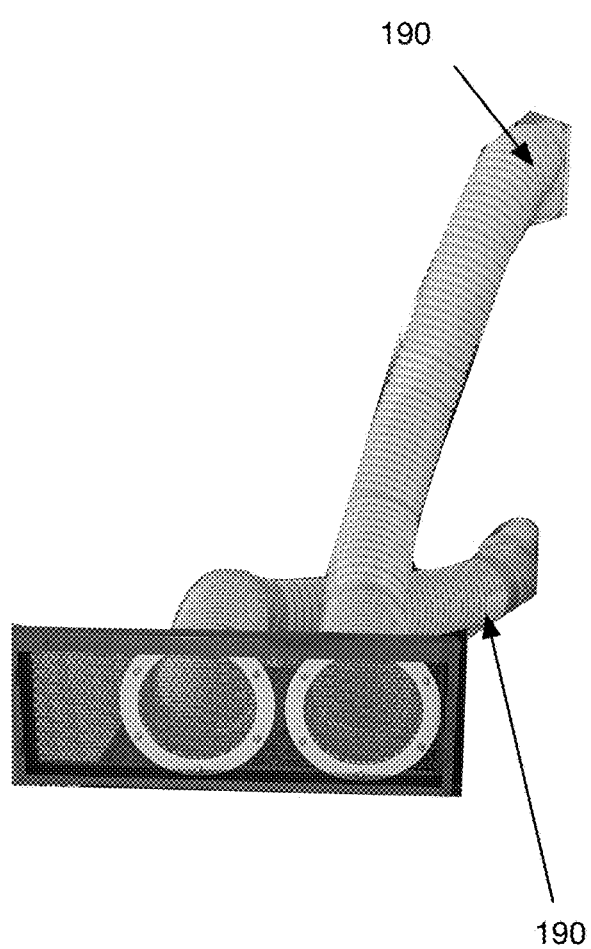
Figure 13:
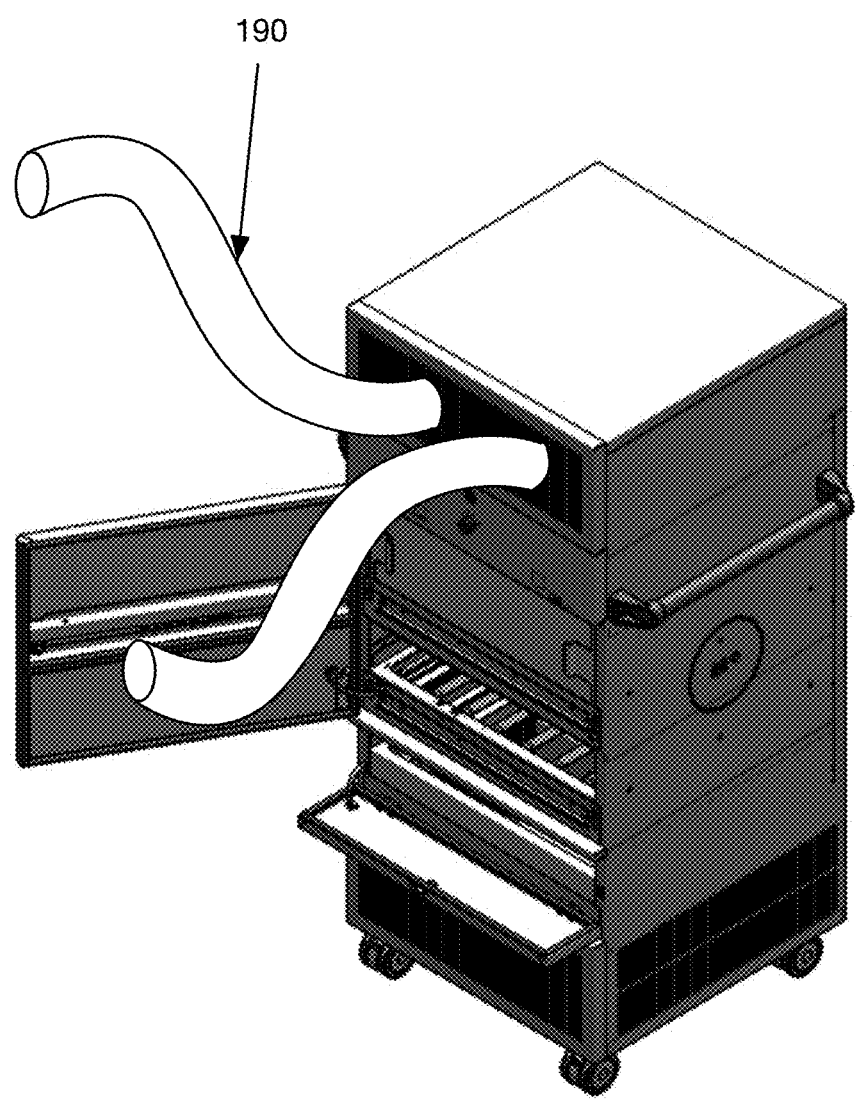
FIG. 13 is a schematic example of a fluid manifold connected to the system.

The system can optionally include one or more fluid manifolds that function to connect the housing interior to one or more pressure sources (examples shown in FIG. 12A, FIG. 12B, FIG. 13). The pressure source can be a positive pressure source (e.g., higher pressure than the housing interior, system's ambient environment, etc.; pushes fluid into the system), negative pressure source (e.g., lower pressure than the housing interior, system's ambient environment, etc.; draws fluid from the system), the ambient environment, and/or any other suitable pressure source. The fluid manifold can be connected to: the inlet, the outlet, and/or any other suitable portion of the housing or system. When the system includes multiple fluid manifolds, the multiple fluid manifolds can be connected to the same or different pressure source and/or system component.

Figure 2:
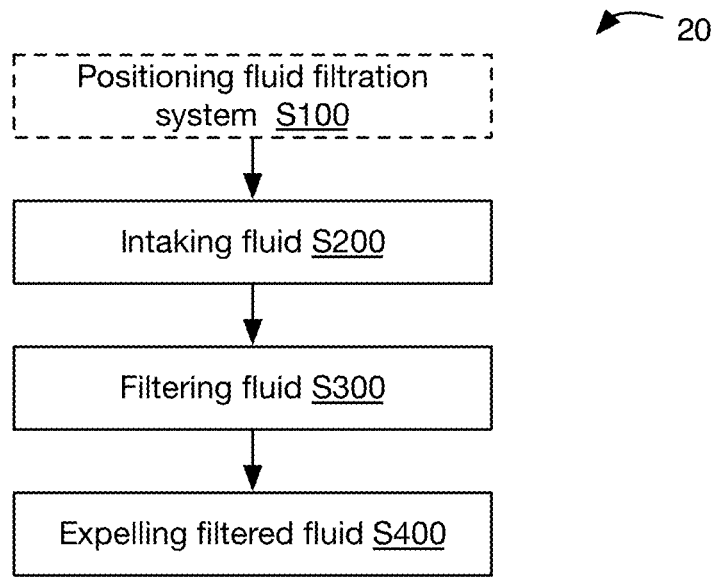
FIG. 2 is a schematic representation of a method of using the system.

In a specific example, as shown in FIG. 2, the method 20 of using the system can include: placing (and orienting) the system within a space (and/or room) S100, intaking fluid S200 (e.g., by operating a flow control mechanism), filtering the fluid S300 (e.g., using a mechanical filter to capture particulates; using an anti-biologic filter to remove biological contaminants; using a sorbent filter to sorb contaminants; using a photocatalytic filter, that has been activated by illuminating the filter with light, to react with contaminants; etc.), and expelling the filtered fluid S400. In variants of this example, filtering the fluid can include selecting the filter(s) to use (e.g., selecting the number, type, orientation, etc.), installing the filter(s) (e.g., order, orientation, locking filters, etc.), and/or any suitable steps. Placing the system within the space can include determining where in a space to place the filter. In a specific example as shown in FIG. 3, the position (and/or orientation such as orientation of intaking air, expelling air, etc.) of the system (e.g., within a room with one or more objects) can be determined using computational fluid dynamics (CFD) analysis of the space. The area of the room and/or space that the system is positioned within (e.g., decontaminates air within) is preferably at least 600 square feet (e.g., 650 ft$^2$, 700 ft$^2$, 750 ft$^2$, 800 ft$^2$, 900 ft$^2$, 1000 ft$^2$, 1200 ft$^2$, 1500 ft$^2$, 2000 ft$^2$, values or ranges therebetween, etc.), but can be less than 600 square feet. However, the position (and/or orientation of the system can be determined empirically, using machine learning, and/or using any suitable method.

4. Illustrative Examples

Figure 5:
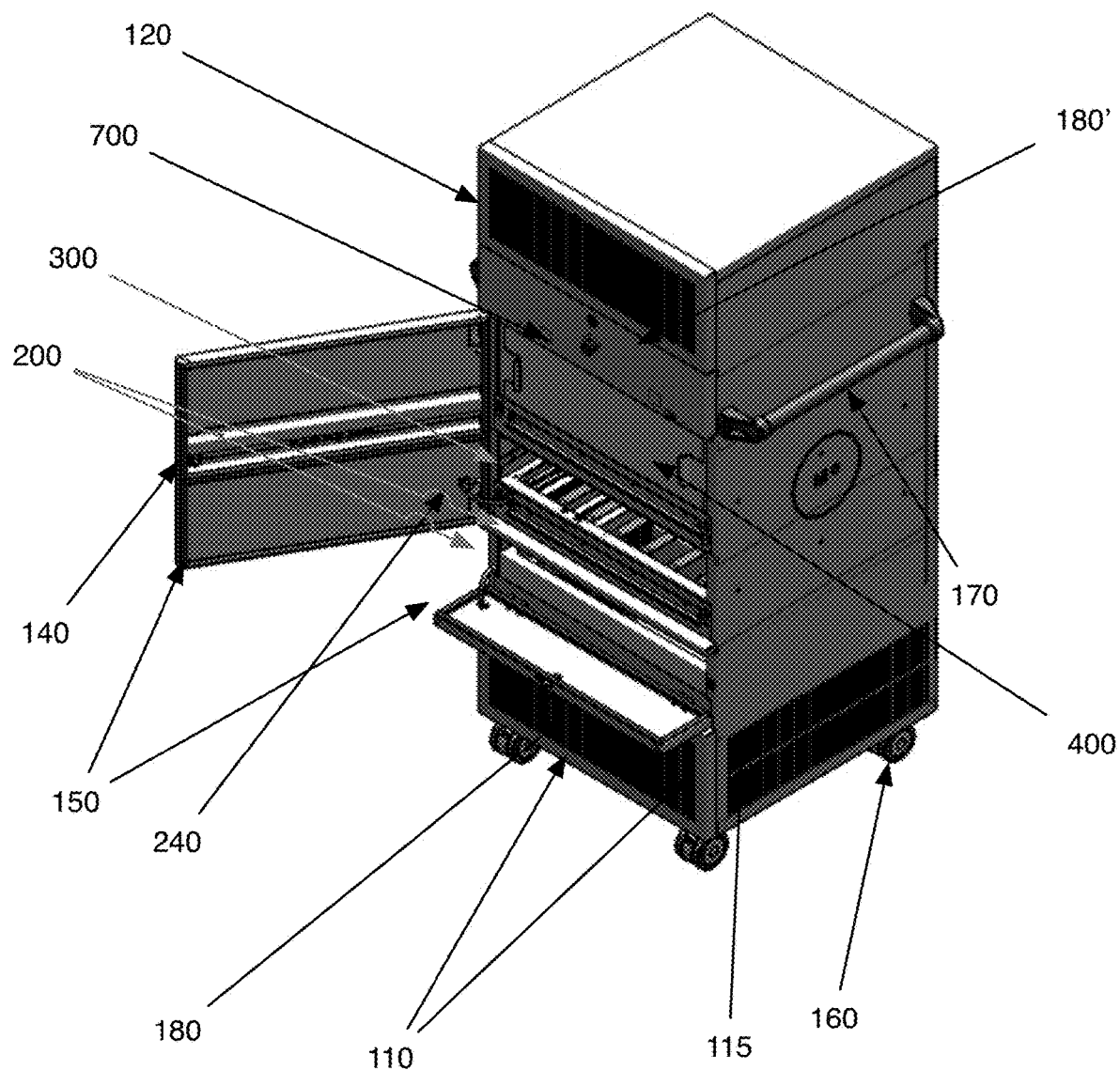
FIG. 5 is a schematic representation of an example of a fluid filtration system.

In an example of the system as shown in FIG. 5 the housing can be substantially a rectangular prism. The inlet of the housing can be arranged on three faces (e.g., a 'front' and the two adjacent sides) of the housing, proximal the bottom of the housing. The inlet can include vents. The housing can define a volume inside the inlet (e.g., an 'inlet volume' 180) wherein the inlet volume enables the pressure of air drawn into the system to equilibrate and stabilize. In this example, the power supply can be mounted within the inlet volume. The power supply can be along the back of the system (e.g., the side of the housing opposing the front of the housing across the lumen and/or inlet volume). The wiring compartment can be along a corner of the housing proximal the power supply. The wiring compartment can include access ports for coupling components to the power supply (via wires). A prefilter (e.g., a mechanical filter) can be installed above the inlet volume. A PECO filter can be installed above the prefilter. The PECO layer of the PECO filter can be arranged to face upward. However, the PECO filter can be oriented in any suitable manner. The prefilter and PECO filter are preferably rectangular with a substantially equal surface area (e.g., pleated area, apparent area of the respective broad face, etc.), but can alternatively have different surface areas. The prefilter and PECO filter preferably have substantially the same as the area of the bottom (and/or top) of the housing, or be smaller (e.g., 99%, 90%, 80%, etc. of the housing transverse cross section). The prefilter and PECO filter are preferably arranged in parallel (e.g., orthogonal to the flow axis), but can alternatively be arranged at an angle to each other or otherwise arranged. The prefilter and PECO filter are preferably each retained within the housing via tracks wherein the filters fit on the respective tracks. Each of the filters is preferably locked in place by compressing the filters (and/or tracks) against a gasket 140, wherein the compression can be supplied by one or more springs (e.g., operated by a knob, dial, key, etc.). Each of the filters can be released (e.g., to facilitate filter replacement, filter reorientation, etc.) by releasing the compression. When the filters are compressed against the gasket, the fluid flow is preferably urged through the filter (e.g., rather than around the filter). A light source can be arranged above or below the PECO filter. The light source is preferably configured to illuminate the PECO filter. The light source can generate UV, visible, and/or any suitable radiation. The filters and light source can be accessed by a door of the housing (e.g., a door in the front of the housing). A flow control mechanism can be arranged above the PECO filter. The outlet of the housing can be proximal to the flow control mechanism. The outlet can include vents (and/or other structures) that can be configured and/or adjusted to modify the speed, direction, turbulence, and/or any suitable flow property for the expelled fluid. The housing can define an outlet volume 180', wherein the outlet volume can enable the filtered air pressure to equilibrate.

However, the system can be arranged in any suitable manner.

It should be noted that where coordinate systems and terminology related to relative orientation(s) are used herein, such terminology shall not be construed as referenced to global coordinates and/or orientations except where appropriate and/or explicit. For example, a system component having a "top" and/or "bottom" shall not be construed as having a particular orientation in relation to a gravity vector except as appropriate and/or explicit. Similarly, "vertical" and/or "horizontal" directions in relation to system components shall not be construed as having a particular orientation in relation to a gravity vector except as appropriate and/or explicit.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. An air filtration system comprising:
   a housing defining an inlet, an outlet, and an air flow path between the inlet and outlet;
   an impeller proximal the outlet configured to draw air into the housing through the inlet and expel air from the housing through the outlet;
   a first photocatalytic filter comprising a photocatalytic material disposed on a substrate, the first photocatalytic filter comprising a first MERV rating;
   a second photocatalytic filter, downstream of the first photocatalytic filter along the air flow path, comprising the photocatalytic material disposed on a second substrate, wherein the second photocatalytic filter comprises a second MERV rating;
   a third photocatalytic filter, downstream of the second photocatalytic filter along the air flow path, comprising the photocatalytic material disposed on a third substrate, wherein the third photocatalytic filter comprises a third MERV rating;
   a first light strip between the first photocatalytic filter and the second photocatalytic filter, wherein the first light strip comprises a first set of light emitting diodes directed toward the first photocatalytic filter and a second set of light emitting diodes directed toward the second photocatalytic filter;
   a second light strip between the second photocatalytic filter and the third photocatalytic filter, wherein the second light strip comprises a first set of light emitting diodes directed toward the second photocatalytic filter and a second set of light emitting diodes directed toward the third photocatalytic filter; and
   a power supply configured to provide electrical power to the first light strip, the second light strip, and the impeller, wherein the power supply is sealed and releases less than a threshold quantity of volatile organic compounds.

2. The air filtration system of claim 1, further comprising a multilayer filter comprising a photoelectrochemical oxidation layer and a sorbent layer, wherein the multilayer filter is downstream of the third photocatalytic filter along the air flow path.

3. The air filtration system of claim 2, further comprising a third light strip comprising a light emitter directed toward the photoelectrochemical oxidation layer.

4. The air filtration system of claim 2, wherein the multilayer filter comprises a particle trapping layer between the photoelectrochemical oxidation layer and the sorbent layer, wherein the multilayer filter comprises a MERV rating that is between about 12 and 16.

5. The air filtration system of claim 1, wherein the photocatalytic material of the first photocatalytic filter is electrically coupled to an electrically conductive support material, wherein the photocatalytic material of the second photocatalytic filter is electrically coupled to a second electrically conductive support material, and wherein the photocatalytic material of the third photocatalytic filter is electrically coupled to a third electrically conductive support material.

6. The air filtration system of claim 1, wherein the first MERV rating is between 8 and 12, wherein the second MERV rating is between 10 and 14, and wherein the third MERV rating is between 12 and 17.

7. The air filtration system of claim 6, wherein the third substrate is associated with a MERV rating between 11 and 16, wherein the third MERV rating is obtained by coating the third substrate with the photocatalytic material.

8. The air filtration system of claim 1, wherein the first light strip is operable to provide visible radiation and wherein the second light strip is operable to provide ultraviolet illumination.

9. An air filtration system comprising:
a housing defining an inlet, an outlet, and an air flow path between the inlet and outlet;
an impeller proximal the outlet configured to draw contaminant-laden air into the housing through the inlet and expel purified air from the housing through the outlet;
a photocatalytic prefilter comprising photocatalytic material disposed on a substrate and a metal mesh electrically coupled to the photocatalytic material;
a multilayer filter, downstream of the photocatalytic prefilter along the air flow path, the multilayer filter comprising:
a photocatalytic layer; and
a sorption layer comprising activated carbon disposed between a pair of scrims; and
a plurality of light strips arranged between the photocatalytic prefilter and the multilayer filter, wherein a first light strip of the plurality of light strips comprises a light emitter directed toward the photocatalytic prefilter and wherein a second light strip of the plurality of light strips comprises a second light emitter directed toward the multilayer filter; and
a power supply configured to provide electrical power to the plurality of light strips and the impeller, wherein the power supply is sealed and releases less than a threshold quantity of volatile organic compounds.

10. The air filtration system of claim 9, wherein the photocatalytic layer of the multilayer filter is the layer of the multilayer filter closest to the plurality of light strips.

11. The air filtration system of claim 9, wherein the photocatalytic prefilter is separated from the plurality of light strips by a first distance and wherein the multilayer filter is separated from the plurality of light strips by a second distance.

12. The air filtration system of claim 11, wherein the second distance is less than the first distance.

13. The air filtration system of claim 9, further comprising a second photocatalytic prefilter arranged between the photocatalytic prefilter and the multilayer filter.

14. The air filtration system of claim 13, further comprising a second plurality of light strips, wherein light emitters of the second plurality of light strips are configured to illuminate at least one of the photocatalytic prefilter, the second photocatalytic prefilter, and the multilayer filter.

15. The air filtration system of claim 13, wherein the photocatalytic prefilter is illuminated with at most a threshold intensity of light, wherein the second photocatalytic prefilter is illuminated with at least the threshold intensity of light.

16. The air filtration system of claim 13, wherein the photocatalytic prefilter comprises a MERV rating between 8 and 12, wherein the second photocatalytic prefilter comprises a MERV rating between 10 and 14.

17. The air filtration system of claim 9, wherein the photocatalytic layer comprises the photocatalytic material.

18. The air filtration system of claim 9, wherein the contaminant-laden air comprises a volatile organic compound (VOC) concentration greater than about 0.1 ppm.

19. The air filtration system of claim 18, wherein the contaminant-laden air comprises terpenes.

20. The air filtration system of claim 9, wherein the purified air comprises a volatile organic compound (VOC) concentration that is at most 10% of a VOC concentration in the contaminant-laden air.

21. The air filtration system of claim 9, wherein at least one of the photocatalytic prefilter or the multilayer filter is secured to the housing by a cam and follower mechanism.

22. The air filtration system of claim 9, wherein the first light strip is operable to provide light with visible wavelengths and the second light strip is operable to provide light with UV-A wavelengths.

* * * * *